(12) United States Patent
Bonny et al.

(10) Patent No.: US 11,457,980 B2
(45) Date of Patent: Oct. 4, 2022

(54) ACTIVE ROBOTIC PIN PLACEMENT

(71) Applicant: THINK SURGICAL, INC., Fremont, CA (US)

(72) Inventors: Daniel P. Bonny, Fremont, CA (US); Joel Zuhars, Fremont, CA (US); Stephen M. Howell, Fremont, CA (US); Timothy Pack, Fremont, CA (US); Kyle Kuznik, Fremont, CA (US); Babak Kianmajd, Fremont, CA (US)

(73) Assignee: THINK SURGICAL, INC., Fremont, CA (US)

( * ) Notice: Subject to any disclaimer, the term of this patent is extended or adjusted under 35 U.S.C. 154(b) by 55 days.

(21) Appl. No.: 15/778,811

(22) PCT Filed: Nov. 15, 2016

(86) PCT No.: PCT/US2016/062020
§ 371 (c)(1),
(2) Date: May 24, 2018

(87) PCT Pub. No.: WO2017/091380
PCT Pub. Date: Jun. 1, 2017

(65) Prior Publication Data
US 2018/0344409 A1      Dec. 6, 2018

Related U.S. Application Data

(60) Provisional application No. 62/349,562, filed on Jun. 13, 2016, provisional application No. 62/259,487, filed on Nov. 24, 2015.

(51) Int. Cl.
*A61B 34/20* (2016.01)
*A61B 34/30* (2016.01)
(Continued)

(52) U.S. Cl.
CPC ............ *A61B 34/20* (2016.02); *A61B 17/155* (2013.01); *A61B 17/157* (2013.01);
(Continued)

(58) Field of Classification Search
CPC . A61B 17/155; A61B 17/157; A61B 17/1764; A61B 2034/102;
(Continued)

(56) References Cited

U.S. PATENT DOCUMENTS 5,086,401 A    2/1992  Glassman et al.
5,234,433 A    8/1993  Bert et al.
(Continued)

FOREIGN PATENT DOCUMENTS

CN    104739487 A    7/2015
EP    0791334 A1    8/1997
(Continued)

OTHER PUBLICATIONS

International Search Report and Written Opinion, dated Jul. 1, 2019, reference 29678 PT-EP.
(Continued)

*Primary Examiner* — Mark D Remaly
(74) *Attorney, Agent, or Firm* — Blue Filament Law PLLC

(57) ABSTRACT

Systems and methods for creating planar cuts on a bone are provided utilizing one or more cutting guides assembled to a plurality of bone pins, where the bone pins are inserted on the bone coincident with one or more virtual pin planes defined relative to one or more of the planar cuts. Alignment guides are also disclosed herein that aid in the creation of pilot holes for receiving a cutting block in a desired position and orientation (POSE). An articulating surgical device actively positions the bone pins coincident with the virtual plane to ensure the cutting guides, when assembled to the (Continued)

pins, aligns one or more guide slots in the desired POSE to create the planar cuts.

17 Claims, 21 Drawing Sheets

(51) Int. Cl.
    *A61B 34/10*     (2016.01)
    *A61B 17/15*     (2006.01)
    *A61B 17/17*     (2006.01)
    *A61B 90/35*     (2016.01)
    *A61B 90/00*     (2016.01)

(52) U.S. Cl.
    CPC .......... *A61B 17/1764* (2013.01); *A61B 34/10* (2016.02); *A61B 34/30* (2016.02); *A61B 90/35* (2016.02); *A61B 2034/102* (2016.02); *A61B 2034/105* (2016.02); *A61B 2034/108* (2016.02); *A61B 2034/2048* (2016.02); *A61B 2034/2055* (2016.02); *A61B 2034/2057* (2016.02); *A61B 2090/3937* (2016.02)

(58) Field of Classification Search
    CPC ........ A61B 2034/105; A61B 2034/108; A61B 2034/2048; A61B 2034/2055; A61B 2034/2057; A61B 2090/3937; A61B 34/10; A61B 34/20; A61B 34/30; A61B 90/35
    See application file for complete search history.

(56) References Cited

U.S. PATENT DOCUMENTS

| | | | |
|---|---|---|---|
| 5,364,402 | A | 11/1994 | Mumme et al. |
| 5,474,559 | A | 12/1995 | Bertin et al. |
| 5,676,668 | A | 10/1997 | McCue et al. |
| 5,709,689 | A | 1/1998 | Ferrante et al. |
| 5,951,475 | A | 9/1999 | Gueziec et al. |
| 6,033,415 | A | 3/2000 | Mittelstadt et al. |
| 6,061,644 | A | 5/2000 | Leis |
| 6,322,567 | B1 | 11/2001 | Mittelstadt et al. |
| 6,723,106 | B1 | 4/2004 | Charles et al. |
| 6,757,582 | B2 | 6/2004 | Brisson et al. |
| 7,043,961 | B2 | 5/2006 | Pandey et al. |
| 7,206,626 | B2 | 4/2007 | Quaid, III |
| 7,346,417 | B2 | 3/2008 | Luth et al. |
| 7,392,076 | B2 | 6/2008 | Moctezuma de La Barrera |
| 8,287,522 | B2 | 10/2012 | Moses et al. |
| 8,560,047 | B2 | 10/2013 | Haider et al. |
| 8,876,830 | B2 | 11/2014 | Hodorek et al. |
| 8,961,536 | B2 | 2/2015 | Nikou et al. |
| 9,060,794 | B2 | 6/2015 | Kang et al. |
| 9,119,638 | B2 | 9/2015 | Schwarz et al. |
| 9,599,624 | B2 | 1/2017 | Philipp |
| 9,561,082 | B2 | 7/2017 | Yen et al. |
| 9,707,043 | B2 | 7/2017 | Bozung |
| 9,814,468 | B2 | 11/2017 | Kang et al. |
| 2001/0015636 | A1 | 8/2001 | Yagi et al. |
| 2005/0216032 | A1 | 9/2005 | Hayden |
| 2006/0122617 | A1 | 6/2006 | Lavallee et al. |
| 2007/0034731 | A1 | 2/2007 | Falco |
| 2007/0073306 | A1 | 3/2007 | Lakin et al. |
| 2007/0156157 | A1 | 7/2007 | Nahum et al. |
| 2007/0288030 | A1 | 12/2007 | Metzger et al. |
| 2008/0009697 | A1 | 1/2008 | Haider et al. |
| 2011/0015636 | A1 | 1/2011 | Katrana et al. |
| 2011/0208256 | A1 | 8/2011 | Zuhars |
| 2011/0245833 | A1 | 10/2011 | Anderson |
| 2012/0123418 | A1 | 5/2012 | Giurgi et al. |
| 2012/0143084 | A1 | 6/2012 | Shoham |
| 2012/0143198 | A1 | 6/2012 | Boyer et al. |
| 2013/0060278 | A1 | 3/2013 | Bozung et al. |
| 2013/0064427 | A1 | 3/2013 | Picard et al. |
| 2013/0261609 | A1 | 10/2013 | Dicorleto et al. |
| 2014/0081275 | A1 | 3/2014 | Metzger et al. |
| 2014/0135791 | A1 | 5/2014 | Nikou et al. |
| 2015/0182285 | A1 | 7/2015 | Yen et al. |
| 2015/0272686 | A1 | 10/2015 | Kang et al. |
| 2015/0320430 | A1 | 11/2015 | Kehres et al. |
| 2016/0030063 | A1 | 2/2016 | Pack et al. |
| 2017/0258532 | A1 | 9/2017 | Shalayev et al. |
| 2018/0014888 | A1 | 1/2018 | Bonny et al. |

FOREIGN PATENT DOCUMENTS

| | | |
|---|---|---|
| EP | 2540238 A1 | 1/2013 |
| EP | 2889015 A1 | 7/2015 |
| EP | 3380032 A4 | 12/2019 |
| JP | H09224953 A | 9/1997 |
| JP | 2005137904 A | 6/2005 |
| JP | 2014504173 A | 2/2014 |
| JP | 2014111181 A | 6/2014 |
| JP | 2015502180 A | 1/2015 |
| WO | 9925420 A1 | 5/1999 |
| WO | 2008/043380 A1 | 4/2008 |
| WO | 201219760 A1 | 8/2012 |
| WO | 2013/063375 A1 | 5/2013 |
| WO | 2015/048319 A1 | 4/2015 |
| WO | 2016049180 A1 | 3/2016 |
| WO | 2016081931 A1 | 5/2016 |
| WO | 2016141378 A1 | 9/2016 |
| WO | 2017091380 A1 | 6/2017 |

OTHER PUBLICATIONS

Taha, Z. et al., "Bone Breakthrough Detection for Orthopedic Robot-Assisted Surgery", APIEMS 2008, Proceedings of the 9th Asia Pacific Industrial Engineering & Management Systems Conference, Dec. 3-5, 2008, Nusa Dua, Bali, Indonesia, pp. 2742-2746.
International Search Report dated Mar. 6, 2017 for International Application No. PCT/US2016/062020 filed Nov. 15, 2016.
Reasons for Rejection issued in corresponding Japanese Patent Appln. No. 2018-513358, dated Oct. 26, 2020.
Examination Report No. 1 issued in corresponding Australian Patent Appln. No. 2016359274, Feb. 10, 2021.
Supplementary European Search Report issued in corresponding European Appln. No. EP16869071, dated Nov. 15, 2019.
U.S. Appl. No. 61/318,537, filed Mar. 29, 2010; Title "Automatically Stabilized Bone Resection Tool", inventors Joel Zuhars and Jody L. Claypool.
Claasen, Gontje C., Martin, Philippe, and Picard, Frederic "High-Bandwidth Low-Latency Tracking Using Optical and Inertial Sensors" Proceedings of the 5th International Conference on Automation, Robotics and Applications, Dec. 6-8, 2011, Wellington, New Zeland; ©2011 IEEE; pp. 366-371.
Claasen, Gontje C., Martin, Philippe, and Picard, Frederic "Optical-Inertial Tracking System with High Bandwith and Low Latency" Proceedings of the 5th International Conference on Automation, Robotics and Applications; ©2011 IEEE; pp. 171-181.
Claasen, G.C., Martin, P., and Picard, F. "Hybrid Optical-Inertial Tracking System For A Servo-Controlled Handheld Tool" Journal of Bone & Joint Surgery, British Volume, www.bjjprocs.boneandjoint.org.uk; dated Aug. 11, 2014; J Bone Joint Surg Br 2012 vol. 94-B No. SUPP XLIV 51; pp. 1/2-2/2.
Claasen, Gontje C., Martin, Philippe, and Picard, Frederic "Tracking and Control for Handheld Surgery Tools"; Biomedical Circuits and Systems Conference (BioCAS), 2011; pp. 428-431; 978-1-4577-1470-2/11/$26.00 ©2011 IEEE.
Brisson, Gabriel, Kanade, Takeo, Digioia, Anthony, and Jaramaz, Branislav "Precision Freehand Sculpting of Bone"; pp. 1-8; The Robotic Institute, Carnegie Mellon University, Pittsburgh PA, USA; (brisson,tk)@cs.cmu.edu; The Institute for Computer Assisted Orthopaedic Surgery, The Western Pennsylvania Hospital, Pittsburgh, PA, USA. (tony, pranko)@icaos.org; C. Barillot, D.R. Haynor, and P. Hellier (Eds.): MICCAI 2004, LNCS 3217, pp. 105-112, 2004, © Springer-Verlag Berlin Heidelberg 2004.

(56) References Cited

OTHER PUBLICATIONS

Tobergte, Andreas, Pomarlan, Mihai, and Hirzinger, Gerd "Robust Multi Sensor Pose Estimation for Medical Applications"; Institute of Robotics and Mechatronics, German Aerospace (DLR), 82234 Wessling, Germany; andreas.tobergte@dlr.de; pp. 105-112.

Kopfle, A., Schill, M., Rautmann, M., Schwarz, M.L.R., Pott, P.P., Wagner, A., Manner, R., Badreddin, E., Weiser, P., and Scharf, H.P. "Occlusion-Robust, Low-Latency Optical Tracking Using a Modular Scalable System Architecture"; Advanced Navigation and Motion Tracking II, Thursday, 17:00, N5; pp. 18.

El-Shenawy, Ahmed, Wagner, Achim, Pott, Peter, Gundling, Ralf, Schwarz, MarKus, Badreddin, Essam "Disturbance Attenuation of a Handheld Parallel Robot"; 2013 IEEE International Conference on Robotics and Automation (ICRA) Karlsruhe, Germany, May 6-10, 2013; pp. 4647-4652; 978-1-4673-5/13/$31.00 @2013 IEEE.

Devos, Thomas, Martin, Philippe, Picard Frederic JM, Borchers, Marco, Cabanial, Nicolas, and Daddier, Aude "A Hand-held computer-controlled tool for total knee replacement"; 5th Annual Meeting of the International Society for Computer Assisted Orthopaedic Surgery CAOS (2005); pp. 88-89.

Wagner, A., Pott, P.P, Scwarz, M.L., Scharf, H.P., Weiser, P., Kopfle, A. Manner, R. and Badreddin, E. "Control of A Handheld Robot For Orthopedic Surgery"; 3rd IFAC 2004; Department of Orthopedic Surgery, Faculty of Clinical Medicine, Mannheim, University Heidelberg, Germany; Institute of CAE, University of Applied Sciences Mannheim, Germany; Institute of Computer Science V, University of Mannheim, Germany; Automation Laboratory, University of Mannheim, Germany; pp. 1-6.

First Office Action issued in corresponding Chinese Patent Appln. No. 201680065658.8, dated Jun. 3, 2020.

Office Action issued in corresponding Japanese Patent Appln. No. 2021-073864, dated May 31, 2022.

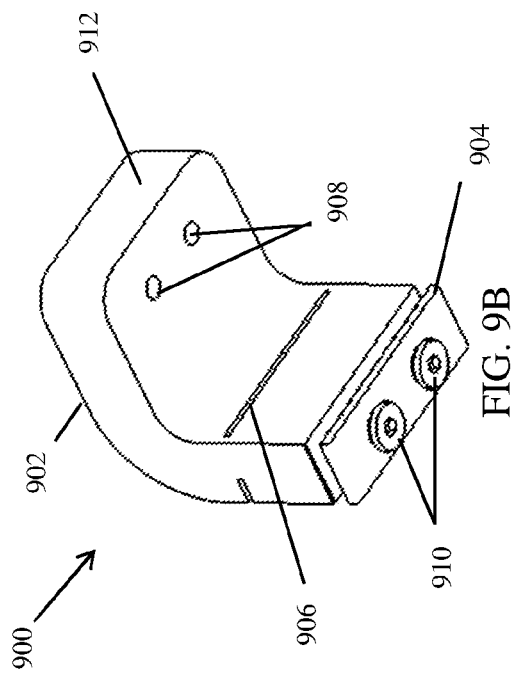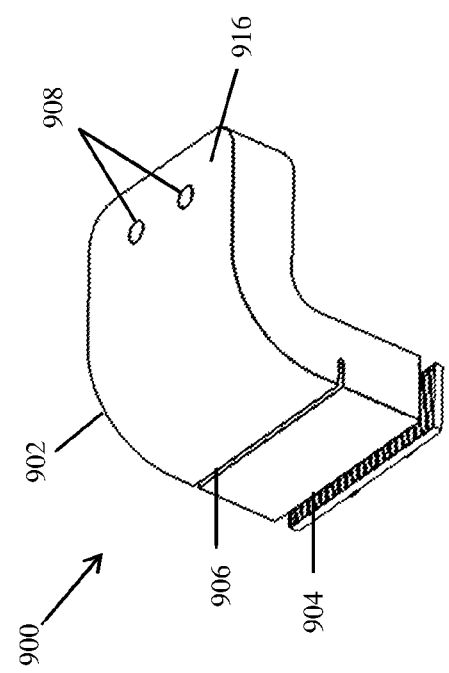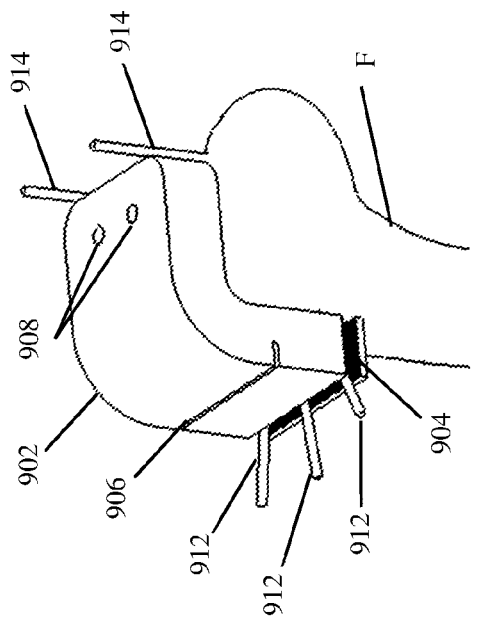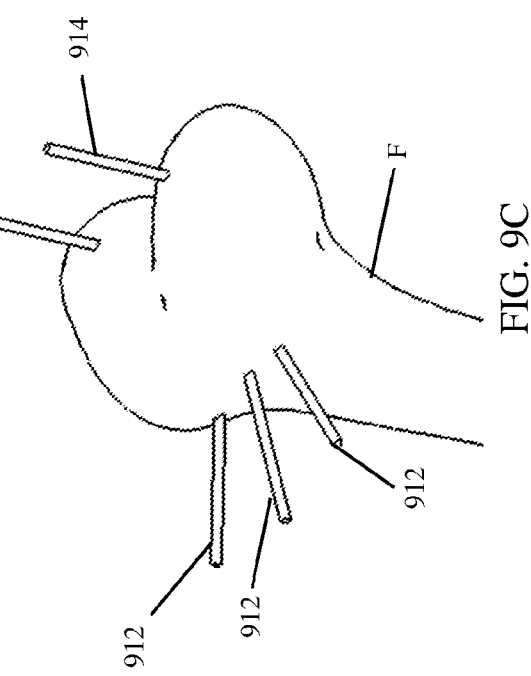

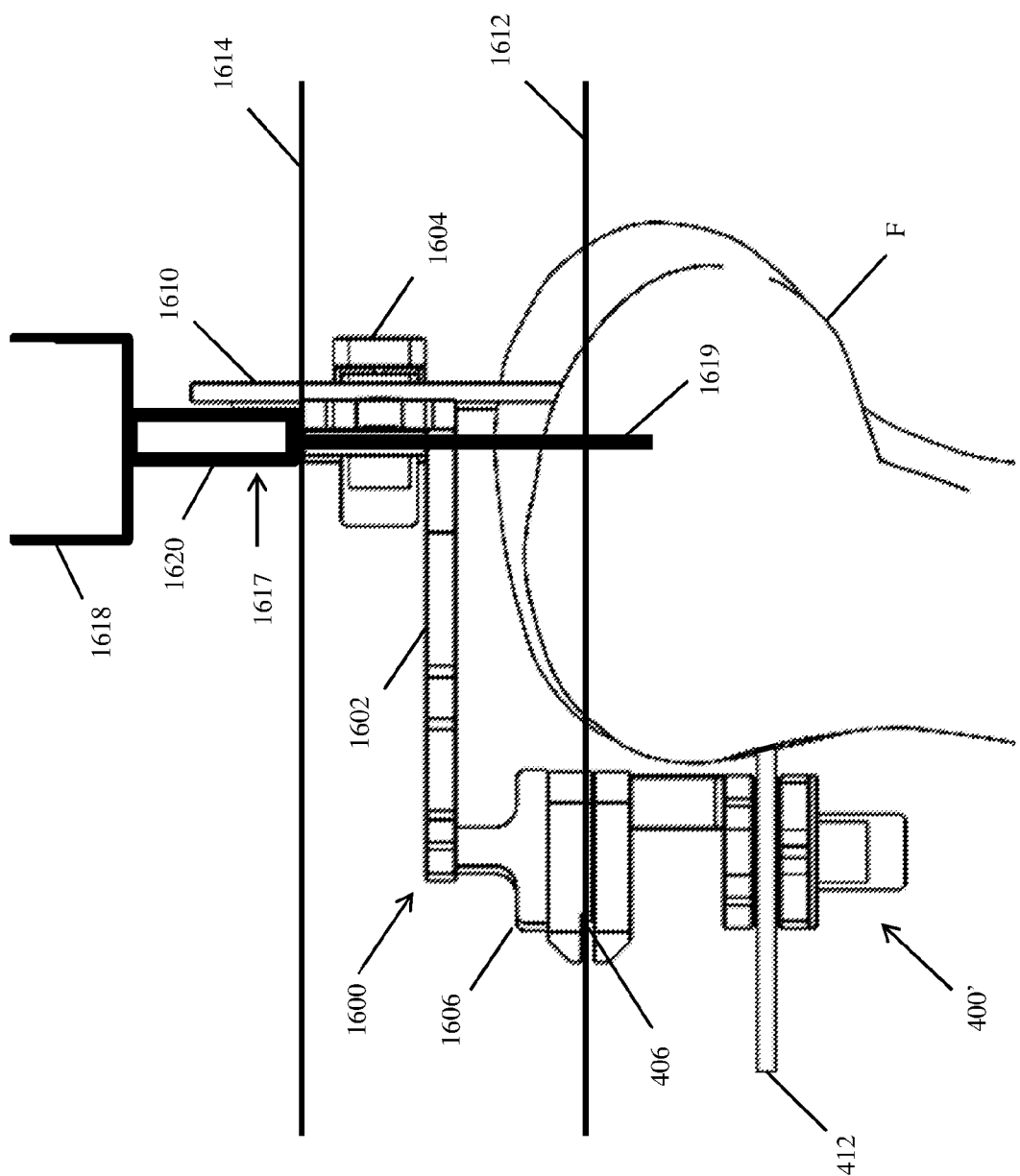

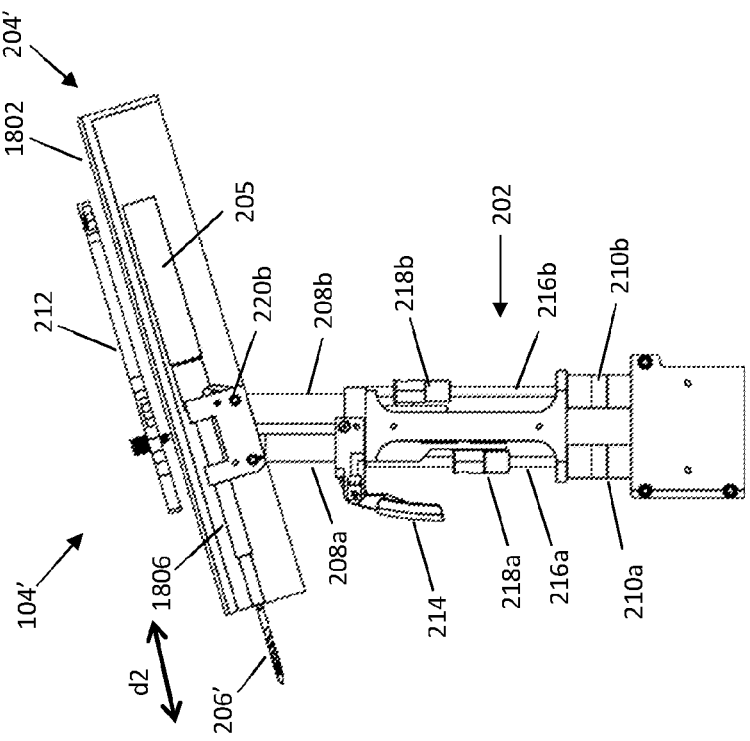
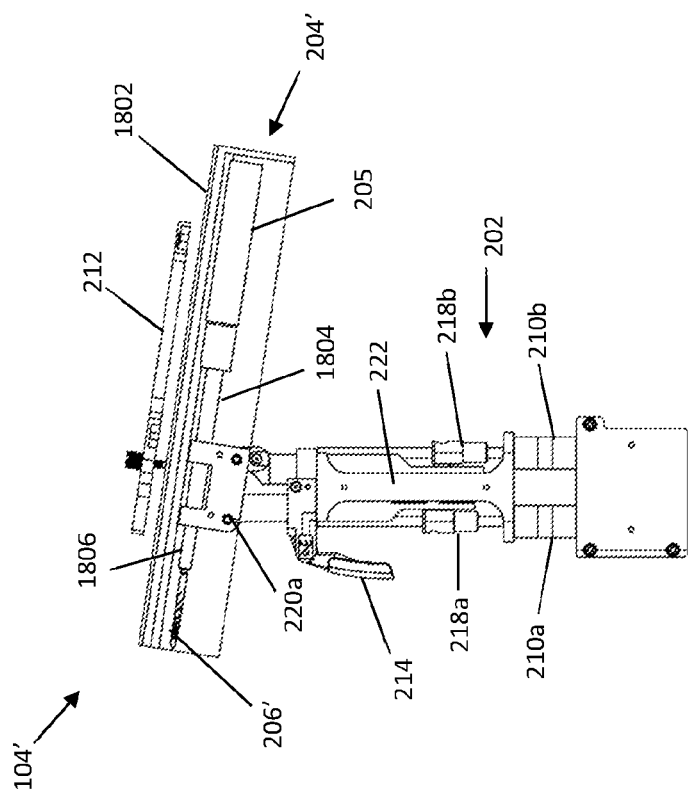
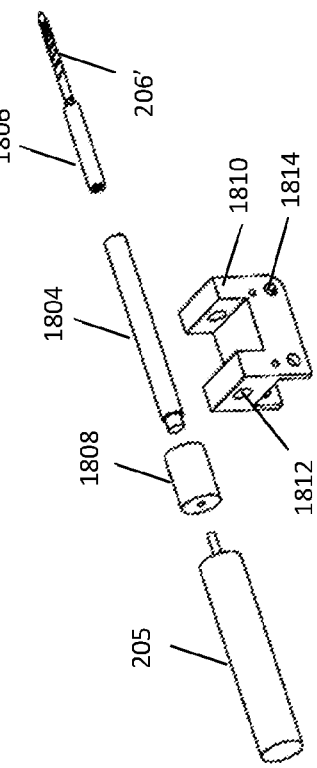
FIG. 18A
FIG. 18B
FIG. 18C

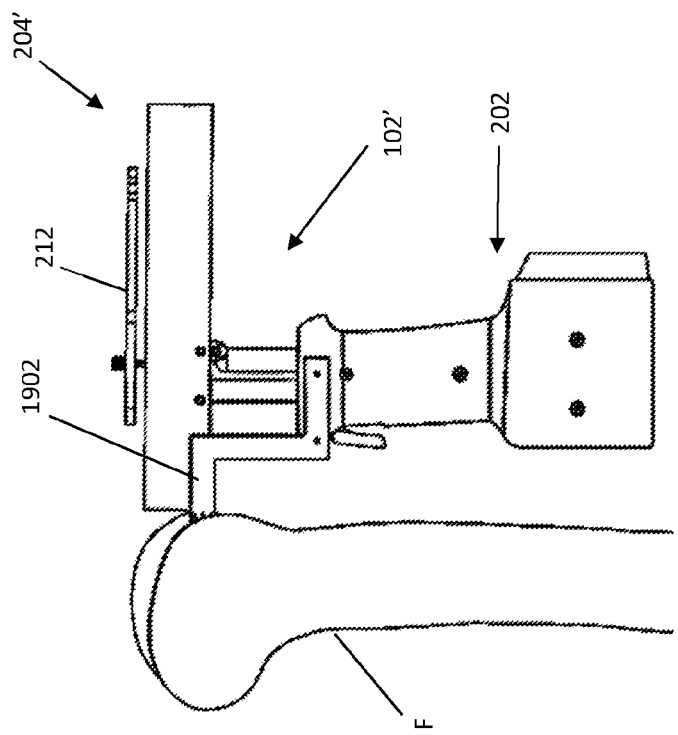
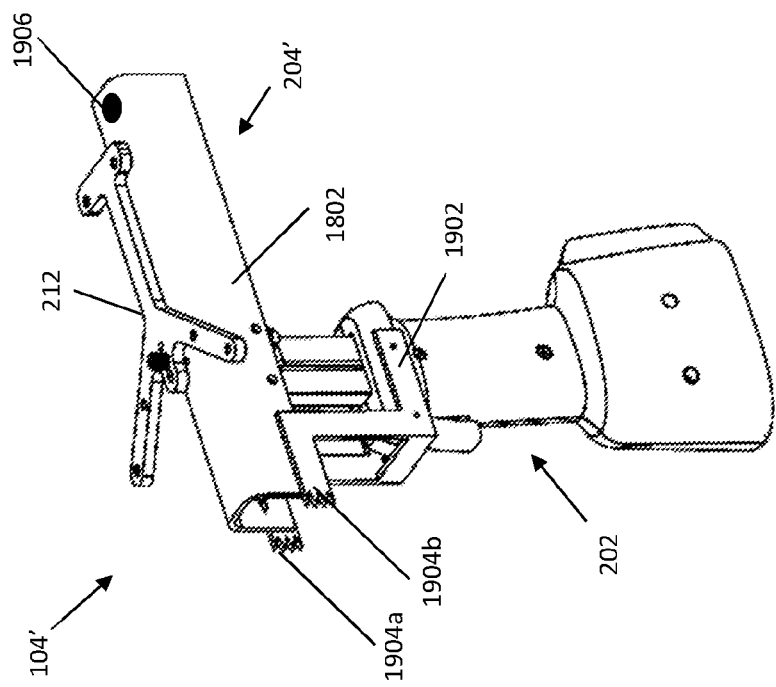
FIG. 19A
FIG. 19B

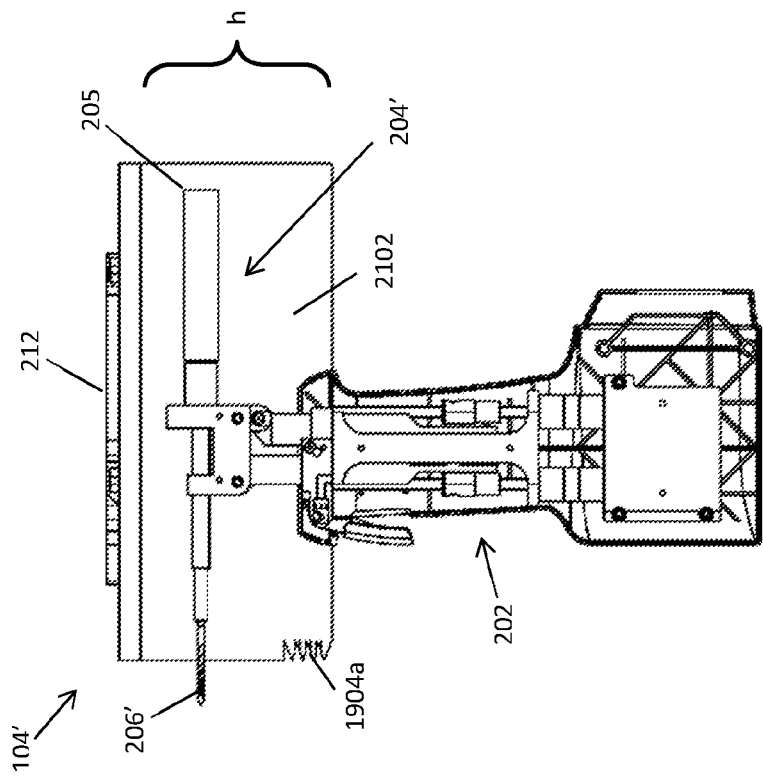
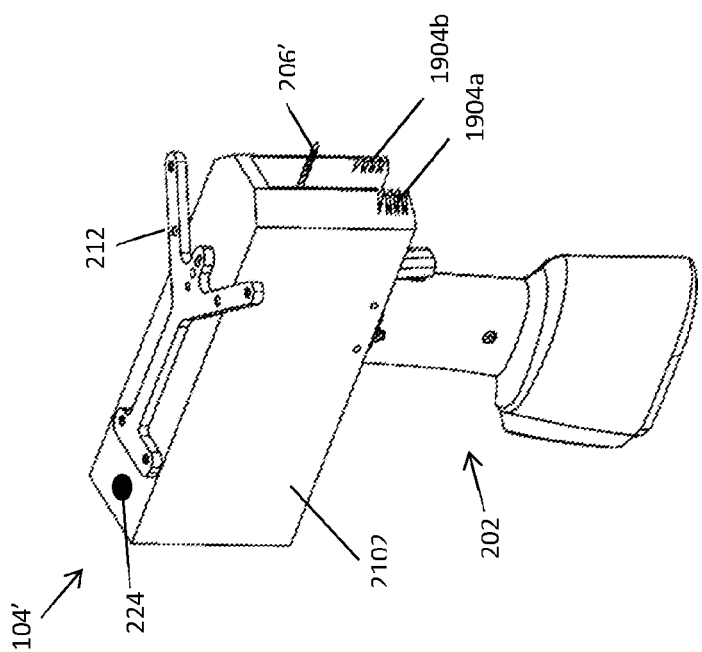

ACTIVE ROBOTIC PIN PLACEMENT

CROSS REFERENCE TO RELATED APPLICATIONS

This application claims priority benefit to U.S. Provisional Application Ser. No. 62/259,487 filed 24 Nov. 2015 and U.S. Provisional Application Ser. No. 62/349,562 filed 13 Jun. 2016; the contents of which are hereby incorporated by reference in their entirety.

FIELD OF THE INVENTION

The present invention generally relates to computer assisted surgery, and more specifically to systems and methods for actively aligning cut guides for total knee arthroplasty.

BACKGROUND

Total knee arthroplasty (TKA) is a surgical procedure in which the articulating surfaces of the knee joint are replaced with prosthetic components, or implants. TKA requires the removal of worn or damaged articular cartilage and bone on the distal femur and proximal tibia. The removed cartilage and bone is then replaced with synthetic implants, typically formed of metal or plastic, to create new joint surfaces.

The position and orientation (POSE) of the removed bone, referred to as bone cuts or resected bone, determines the final placement of the implants within the joint. Generally, surgeons plan and create the bone cuts so the final placement of the implants restores the mechanical axis or kinematics of the patient's leg while preserving the balance of the surrounding knee ligaments. Even small implant alignment deviations outside of clinically acceptable ranges correlates to less than optimal outcomes and increased rates of revision surgery. In TKA, creating the bone cuts to correctly align the implants is especially difficult because the femur requires at least five planar bone cuts to receive a traditional femoral prosthesis. The planar cuts on the distal femur must be aligned in five degrees of freedom to ensure a proper orientation: anterior-posterior translation, proximal-distal translation, external-internal rotation, varus-valgus rotation, and flexion-extension rotation. Any malalignment in any one of the planar cuts or orientations may have drastic consequences on the final result of the procedure and the wear pattern of the implant.

Cutting guides, also referred to as cutting blocks or cutting jigs, are commonly used to aid in creating the bone cuts. The cutting guides include guide slots to restrict or align a bone removal device, such as an oscillating saw, in the correct bone resection plane. Cutting guides are advantageous for several reasons. One such advantage is that the guide slots stabilize the bone removal device during cutting to ensure the bone removal device does not deflect from the desired plane. Second, a single cutting guide may include multiple guide slots (referred to herein as an N-in-1 cutting block) which can define more than one cutting plane to be accurately resected, such as a 4-in-1 block, 5-in-1 block . . . N-in-1 block. Thus, the surgeon can quickly resect two or more planes once the cutting guide is accurately oriented on the bone. Still another advantage is that the guide slots and the working end of the oscillating saw are typically planar in shape and relatively thin, which make them ideal for creating planar bone cuts. The advantages of using a cutting guide are apparent, however, the cutting guide still needs to be accurately positioned on the bone prior to executing the cut. In fact, it is the placement of the guide slots on the bone that remains one of the most difficult, tedious and critical tasks for surgeons during TKA.

Various techniques have been developed to help a surgeon correctly align the guide slots on the bone. Typical cutting guide systems include a number of manual adjustment mechanisms that are used in conjunction with passive navigation, image-guidance, or anatomical landmark referencing. Guide pins are used to temporarily fix the cutting guide in the general orientation on the bone, and additional fine tuning adjustments are then made. One of the main drawbacks however, is the complexity of the cutting guides. The manual adjustment mechanisms are usually quite elaborate since the guide slots need to be oriented in six degrees of freedom. This requires extensive user training, which often predisposes a surgeon to use a particular implant or implant line that is specific for a given cutting guide system even if another implant affords other advantages. Additionally, when orienting the cutting guides using anatomical references, variations of the anatomy from patient to patient may cause difficulty in accurately aligning the cutting guides consistently. Passive navigation and image-guidance may be useful, but the surgeon has to constantly reference a monitor or other feedback mechanism, introducing error and prolonging the operating procedure. A typical total knee arthroplasty procedure may take approximately 60 minutes to complete.

Other methods have also been developed to alleviate the use of cutting guides. Haptic and semi-active robotic systems allow a surgeon to define virtual cutting boundaries on the bone. The surgeon then manually guides a cutting device while the robotic control mechanisms maintain the cutting device within the virtual boundaries. One disadvantage of the robotic system however, is the deflection of the cutting device that may occur when attempting to create a planar cut on the bone. The cutting device may encounter curved surfaces on the bone causing the device to skip or otherwise deflect away from the resection plane. The resulting planar cuts would then be misaligned, or at least difficult to create since the cutting device cannot be oriented directly perpendicular to the curved surface of the bone to create the desired bone cut. Cutting guides on the other hand are removably fixed directly against the bone, and therefore deflection of the cutting device is greatly decreased. In addition, the costs associated with haptic or semi-active robotic systems are considerably higher than manual instrumentation.

Thus, there is a need for a system and method to take advantage of using a cutting guide without the current time consuming and labor intensive burden of orienting the cutting guide on the bone.

SUMMARY OF THE INVENTION

An alignment system for surgical bone cutting procedures includes a plurality of bone pins inserted within a virtual plane relative to a cut plane to be created on a subject's bone, a cutting guide configured to be received onto said plurality of bone pins, and one or more guide slots within said cutting guide, said one or more guide slots configured to guide a surgical saw to make surgical cuts on the subject's bone.

A method for aligning a cutting guide on a subject's bone includes determining one or more cut planes from a surgical plan obtained with planning software. Determining one or more virtual planes relative to each of the one or more cut planes to be created on the subject's bone. Aligning and inserting a plurality of bone pins within a virtual plane from the one or more virtual planes. Attaching a cutting guide configured to clamp onto the plurality of inserted bone pins, and wherein one or more guide slots are within the attached cutting guide, the one or more guide slots configured to guide a surgical saw to make surgical cuts on the subject's bone that correspond to the one or more cut planes.

A surgical device for pin insertion in a subject's bone to aid in performing a bone cutting procedure includes a working portion configured to articulate a pin for insertion in the subject's bone. A hand-held portion pivotably connected to the working portion by a front linear rail and rear linear rail, where the front linear rail and the rear linear rail are actuated by a set of components in the hand-held portion to adjust pitch and translation of the working portion relative to the hand-held portion, the front linear rail and the rear linear rail each having a first end and a second end. A tracking array having a set of three or more fiducial markers rigidly attached the working portion to permit a tracking system to track a position and orientation (POSE) of the working portion. The POSE of the pins upon insertion in the bone being used to assemble and align a cutting guide thereon to facilitate the creation of a desired cut plane.

BRIEF DESCRIPTION OF THE DRAWING

The present invention is further detailed with respect to the following drawings. These figures are not intended to limit the scope of the present invention but rather illustrate certain attribute thereof wherein;

FIGS. 9A and 9B depicts a universal distal cutting guide with a N-in-1 cutting block alignment guide in a top perspective view (FIG. 9A), bottom perspective view (FIG. 9B), and in accordance with embodiments of the invention;

FIG. 9C depicts bone pins positioned in the context of a bone;

FIG. 9D depicts the universal cutting guide with a N-in-1 cutting block alignment guide of FIGS. 9A and 9B secured to bone using the bone pins of FIG. 9C;

FIG. 16E illustrates a stepped diameter drill bit for use with the reference alignment guide in accordance with embodiments of the invention;

FIGS. 18A and 18B depict a cross-section of a articulating pin-driver device, where FIG. 18A depicts the device having a pin in a retracted state, and FIG. 18B depicts the device having a pin in an extended state in accordance with embodiments of the invention;

FIG. 18C is an exploded view that illustrates the components of a working portion of the pin-driver device in accordance with embodiments of the invention;

FIGS. 19A and 19B depicts and illustrate a bone stability member attached to the pin-driver device and the use thereof in accordance with embodiments of the invention;

FIGS. 21A and 21B depicts a full enclosure enclosing the working portion in accordance with embodiments of the invention.

DETAILED DESCRIPTION OF THE INVENTION

The present invention has utility as a system and method to aid a surgeon in efficiently and precisely aligning a cutting guide on a patient's bone. The system and method is especially advantageous for total knee arthroplasty and revision knee arthroplasty, however, it should be appreciated that other medical applications may exploit the subject matter disclosed herein such as high tibial osteotomies, spinal reconstruction surgery, and other procedures requiring the precise placement of a cutting guide to aid a surgeon in creating bone cuts.

The following description of various embodiments of the invention is not intended to limit the invention to these specific embodiments, but rather to enable any person skilled in the art to make and use this invention through exemplary aspects thereof.

Embodiments of the present invention may be implemented with a surgical system. Examples of surgical systems used in embodiments of the invention illustratively include a 1-6 degree of freedom hand-held surgical system, a serial-chain manipulator system, a parallel robotic system, or a master-slave robotic system, as described in U.S. Pat. Nos. 5,086,401, 7,206,626, 8,876,830 and 8,961,536, U.S. Pat. App. No. 2013/0060278, and U.S. Prov. App. No. 62/054,009. In a specific embodiment, the surgical system is a serial-chain manipulator system as described in U.S. Pat. No. 6,033,415 assigned to the assignee of the present application and incorporated by reference herein in its entirety. The manipulator system may provide autonomous, semi-autonomous, or haptic control and any combinations thereof. In a specific embodiment, a tool attached to the manipulator system may be manually maneuvered by a user while the system provides at least one of power, active or haptic control to the tool.

Figure 1:
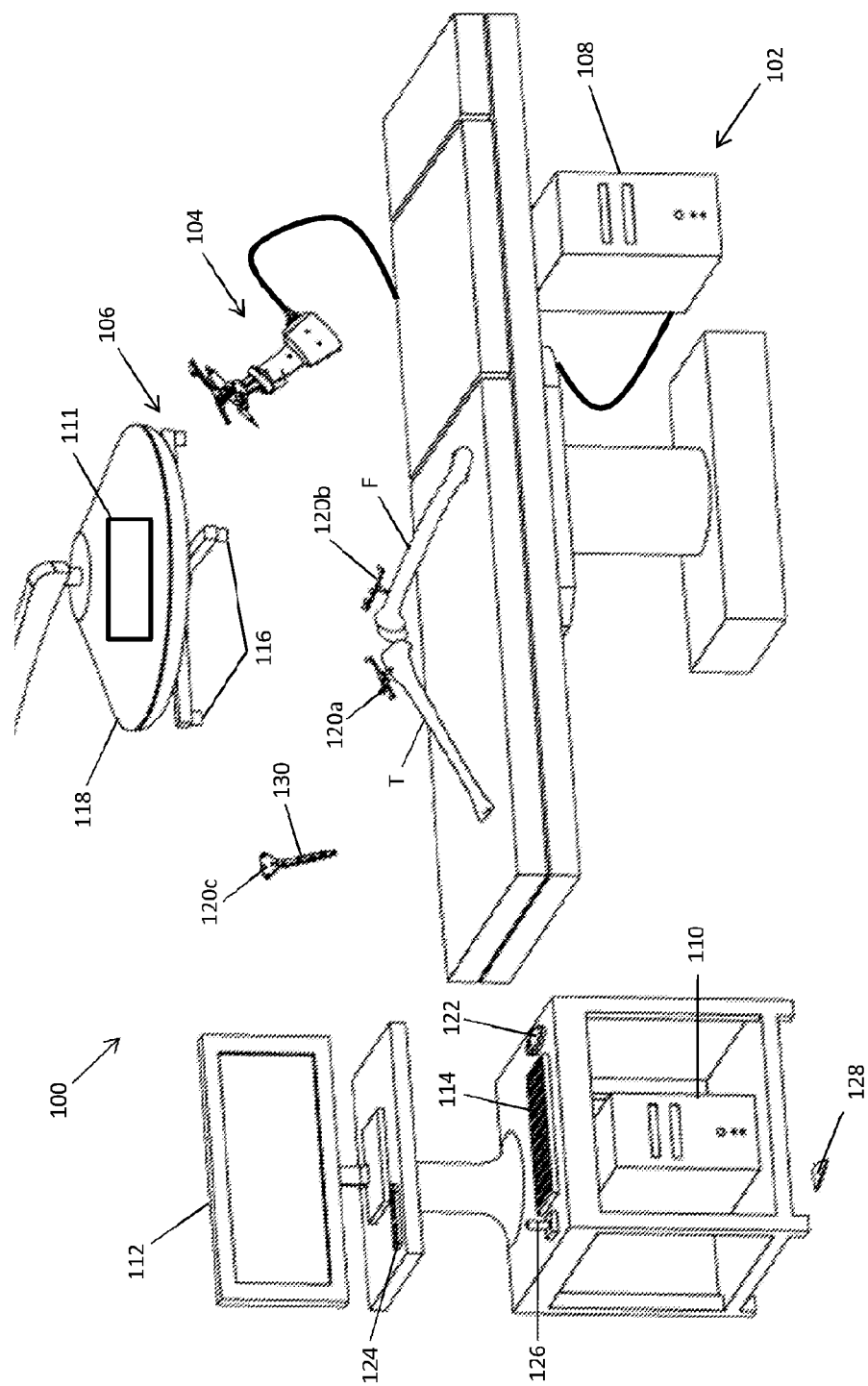
FIG. 1 depicts a surgical system to perform a procedure on a bone.

With reference to the figures, FIG. 1 illustrates a 2-degree-of-freedom (2-DOF) surgical system 100. The 2-DOF surgical system 100 is generally described in PCT App. Num. US2015/051713, assigned to the assignee of the present application and incorporated by reference herein in its entirety. The 2-DOF surgical system 100 includes a computing system 102, an articulating surgical device 104, and a tracking system 106. The surgical system 100 is able to guide and assist a user in accurately placing pins coincident with a virtual pin plane that is defined relative to a subject's bone. The virtual plane is defined in a surgical plan such that a cut guide when assembled to the inserted pins align one or more guide slots with the bone cuts required to receive a prosthetic implant in a planned position and orientation.

Articulating Surgical Device

Figure 2B:
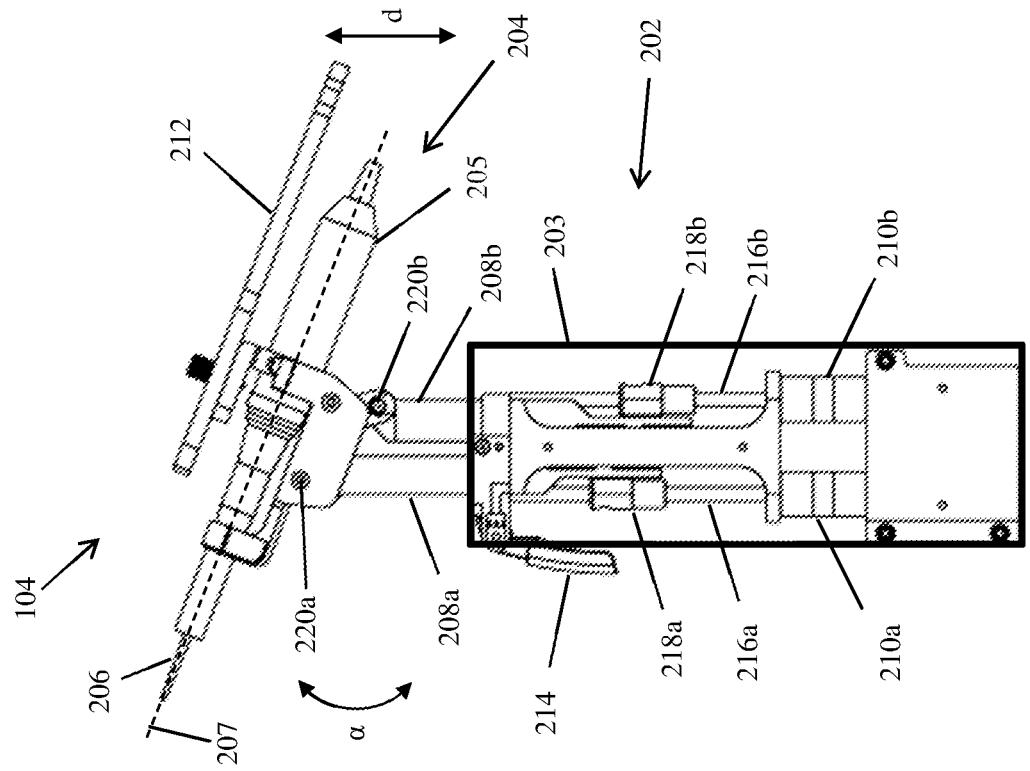
FIGS. 2A and 2B depicts a surgical device used in the surgical system.
Figure 2A:
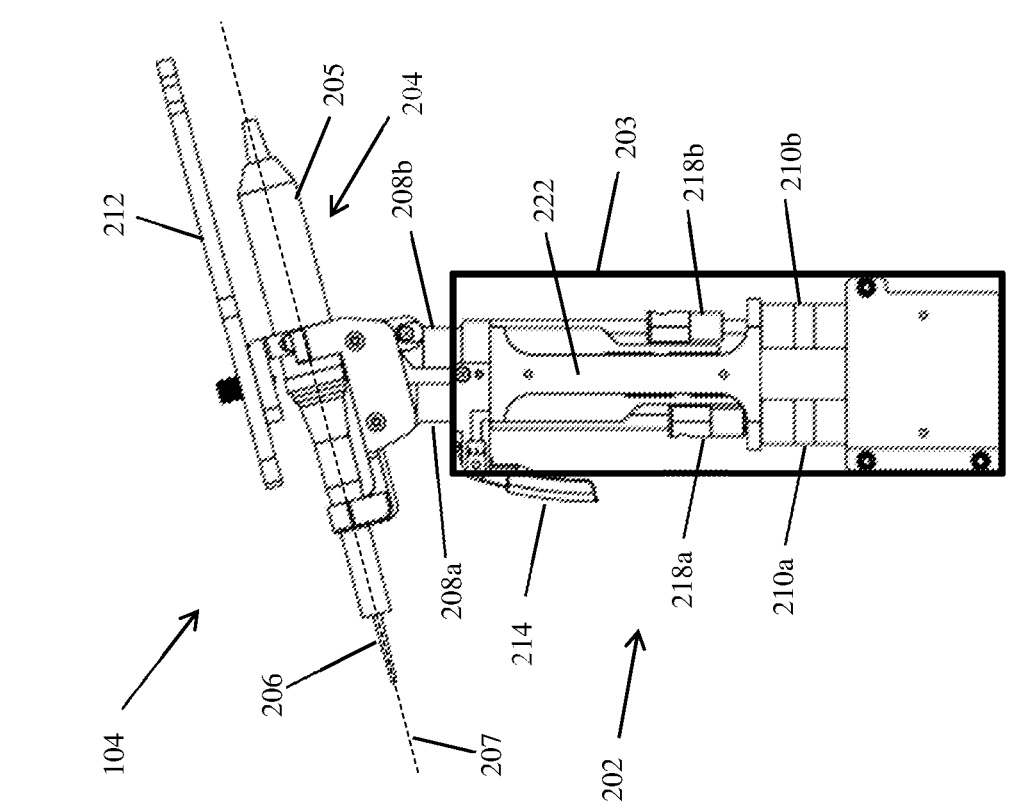

FIGS. 2A and 2B illustrate the articulating surgical device 104 of the 2-DOF surgical system 100 in more detail. The surgical device 104 includes a hand-held portion 202 and a working portion 204. The hand-held portion 202 includes an outer casing 203 of ergonomic design to be held and manipulated by a user. The working portion 204 includes a tool 206 having a tool axis 207. The tool 206 is readily attached to and driven by a motor 205. The hand-held portion 202 and working portion 204 are connected by a front linear rail 208a and a back linear rail 208b that are actuated by components in the hand-held portion 202 to control the pitch and translation of the working portion 204 relative to the hand-held portion 202. A tracking array 212, having three or more fiducial markers, is rigidly attached to the working portion 142 to permit a tracking system 106 to track the POSE of the working portion 204. The fiducial markers may be active markers such as light emitting diodes (LEDs), or passive markers such as retroreflective spheres. An input/output port in some inventive embodiments provides power and/or control signals to the device 104; or the device may receive power from batteries and control signals via a wireless connection alleviating the need for electrical wiring to be connected to the device 104. In a particular embodiment, the device may receive wireless control signals via visible light communication as described in Int'l Pat. App. WO 2016/081931 assigned to the assignee of the present application and incorporated by reference herein in its entirety. The device 104 may further include one or more user input mechanisms such as a trigger 214 or a button.

Within the outer casing of the hand-held portion 202 are a front actuator 210a that powers a front ball screw 216a and a back actuator 210b that powers a back ball screw 216b. The actuators (210a, 210b) may be servo-motors that bi-directionally rotate the ball screws (216a, 216b). A first end of the linear rails (208a, 208b) are attached to the working portion 204 via hinges (220a, 220b), where the hinges (220a, 220b) allow the working portion 204 to pivot relative to the linear rails (208a, 208b). Ball nuts (218a, 218b) are attached at a second end of the linear rails (208a, 208b). The ball nuts (218a, 218b) are in mechanical communication with the ball screws (216a, 216b). The actuators (210a, 210b) power the ball screws (216a, 216b) which cause the ball nuts (218a, 218b) to translate along the axis of the ball screws (216a, 216b). Accordingly, the translation 'd' and pitch 'α' of the working portion 204 may be adjusted depending on the position of each ball nut (218a, 218b) on their corresponding ball screw (216a, 216b). A linear guide 222 may further constrain and guide the motion of the linear rails (208a, 208b) in the translational direction 'd'.

Computing System and Tracking System

With reference back to FIG. 1, the computing system 102 generally includes hardware and software for executing a surgical procedure. In particular embodiments, the computing system 102 provides actuation commands to the actuators (210a, 210b) to control the position and orientation (POSE) of the tool 206. The computing system 102 can thus maintain the tool axis 207 with a virtual plane defined in a surgical plan independent of the POSE of the hand-held portion 202.

The computing system 102 in some inventive embodiments includes: a device computer 108 including a processor; a planning computer 110 including a processor; a tracking computer 111 including a processor, and peripheral devices. Processors operate in the computing system 102 to perform computations associated with the inventive system and method. It is appreciated that processor functions are shared between computers, a remote server, a cloud computing facility, or combinations thereof.

In particular inventive embodiments, the device computer 108 may include one or more processors, controllers, and any additional data storage medium such as RAM, ROM or other non-volatile or volatile memory to perform functions related to the operation of the surgical device 104. For example, the device computer 108 may include software, data, and utilities to control the surgical device 104 such as the POSE of the working portion 204, receive and process tracking data, control the speed of the motor 205, execute registration algorithms, execute calibration routines, provide workflow instructions to the user throughout a surgical procedure, as well as any other suitable software, data or utilities required to successfully perform the procedure in accordance with embodiments of the invention.

The device computer 108, the planning computer 110, and the tracking computer 111 may be separate entities as shown, or it is contemplated that their operations may be executed on just one or two computers depending on the configuration of the surgical system 100. For example, the tracking computer 111 may have operational data to control the device 104 without the need for a device computer 108. Or, the device computer 108 may include operational data to plan to the surgical procedure with the need for the planning computer 110. In any case, the peripheral devices allow a user to interface with the surgical system 100 and may include: one or more user interfaces, such as a display or monitor 112; and various user input mechanisms, illustratively including a keyboard 114, mouse 122, pendent 124, joystick 126, foot pedal 128, or the monitor 112 may have touchscreen capabilities.

The planning computer 110 is preferably dedicated to planning the procedure either pre-operatively or intra-operatively. For example, the planning computer 110 may contain hardware (e.g. processors, controllers, and memory), software, data, and utilities capable of receiving and reading medical imaging data, segmenting imaging data, constructing and manipulating three-dimensional (3D) virtual models, storing and providing computer-aided design (CAD) files, planning the POSE of the implants relative to the bone, generating the surgical plan data for use with the system 100, and providing other various functions to aid a user in planning the surgical procedure. The planning computer also contains software dedicated to defining virtual planes with regards to embodiments of the invention as further described below. The final surgical plan data may include an image data set of the bone, bone registration data, subject identification information, the POSE of the implants relative to the bone, the POSE of one or more virtual planes defined relative to the bone, and any tissue modification instructions. The device computer 108 and the planning computer 110 may be directly connected in the operating room, or may exist as separate entities. The final surgical plan is readily transferred to the device computer 108 and/or tracking computer 111 through a wired or wireless connection in the operating room (OR); or transferred via a non-transient data storage medium (e.g. a compact disc (CD), a portable universal serial bus (USB drive)) if the planning computer 110 is located outside the OR. As described above, the computing system 102 may act as a single entity, with multiple processors, capable of performing the functions of the device computer 108, the tracking computer 111, and the planning computer 110.

The computing system 102 may accurately maintain the tool axis 207 in 3-D space based on POSE data from the tracking system 106 as shown in FIG. 1. The tracking system 106 generally includes a detection device to determine the POSE of an object relative to the position of the detection device. In a particular embodiment, the tracking system 106 is an optical tracking system as described in U.S. Pat. No. 6,061,644, having two or more optical receivers 116 to detect the position of fiducial markers arranged on rigid bodies. Illustrative examples of the fiducial markers include: an active transmitter, such as an LED or electromagnetic radiation emitter; a passive reflector, such as a plastic sphere with a retroreflective film; or a distinct pattern or sequence of shapes, lines or other characters. A set of fiducial markers arranged on a rigid body is referred to herein as a fiducial marker array (120a, 120b, 120c, 212), where each fiducial marker array (120a, 120b, 120c, 212) has a unique geometry/arrangement of fiducial markers, or a unique transmitting wavelength/frequency if the markers are active LEDS, such that the tracking system 106 can distinguish between each of the tracked objects. In a specific embodiment, the fiducial marker arrays (120a, 120b, 120c, 212) include three or more active emitters or passive reflectors uniquely arranged in a known geometry on each rigid body.

The tracking system 106 may be built into a surgical light 118, located on a boom, stand, or built into the walls or ceilings of the operating room. The tracking system computer 111 includes tracking hardware, software, data, and utilities to determine the POSE of objects (e.g. bones such as the femur F and tibia T, the surgical device 104) in a local or global coordinate frame. The POSE of the objects is referred to herein as POSE data, where this POSE data is readily communicated to the device computer 108 through a wired or wireless connection. Alternatively, the device computer 108 may determine the POSE data using the position of the fiducial markers detected directly from the optical receivers 116.

The POSE data is determined using the position of the fiducial markers detected from the optical receivers 116 and operations/processes such as image processing, image filtering, triangulation algorithms, geometric relationship processing, registration algorithms, calibration algorithms, and coordinate transformation processing.

POSE data from the tracking system 106 is used by the computing system 102 to perform various functions. For example, the POSE of a digitizer probe 130 with an attached probe fiducial marker array 120c may be calibrated such that tip of the probe is continuously known as described in U.S. Pat. No. 7,043,961. The POSE of the tip or axis of the tool 206 may be known with respect to the device fiducial marker array 212 using a calibration method as described in Int'l Pat. App. No. WO 2016/141378. Registration algorithms are readily executed using the POSE data to determine the POSE and/or coordinate transforms between a bone, a surgical plan, and a surgical system. For example, in registration methods as described in U.S. Pat. Nos. 6,033,415 and 8,287,522, points on a patient's bone may be collected using a tracked digitizer probe to transform the coordinates of a surgical plan, coordinates of the bone, and the coordinates of a surgical device, The bone may also be registered using image registration as described in U.S. Pat. No. 5,951,475. The coordinate transformations may be continuously updated using the POSE data from a tracking system tracking the POSE of the bone post-registration and the surgical device.

It should be appreciated that in certain inventive embodiments, other tracking systems are incorporated with the surgical system 100 such as an electromagnetic field tracking system, ultrasound tracking systems, accelerometers and gyroscopes, or a mechanical tracking system. The replacement of a non-mechanical tracking system with other tracking systems should be apparent to one skilled in the art. In specific embodiments, the use of a mechanical tracking system may be advantageous depending on the type of surgical system used such as the one described in U.S. Pat. No. 6,322,567 assigned to the assignee of the present application and incorporated by reference in its entirety.

In the surgical system 100, an optical tracking system 106 with optical receivers 116 is used to collect POSE data of the femur and tibia during total knee arthroplasty. The distal femur F and proximal tibia T are exposed as in a typical TKA procedure. Tracking arrays 120a and 120b are attached thereto and the femur F and tibia T are subsequently digitized and registered to a surgical plan. The POSE of the femur F and tibia T are tracked in real-time by the tracking system 106 so the coordinate transformation between the surgical plan and the surgical device are updated as the bones and surgical device move in the operating space. Therefore, a relationship between the POSE of the tool 206 and the POSE of any coordinates defined in the surgical plan may be determined by the computing system 102. In turn, the computing system 102 can supply actuation commands to the actuators (210a, 210b) in real-time to accurately maintain the tool axis 207 to the defined coordinates.

Additionally, user input mechanisms, such as the trigger 214 or foot pedal 128, may be used by the user to indicate to the computing system 102 that the tool axis 207 needs to be maintained to other coordinates defined in a surgical plan. For example, the tool axis 207 may be maintained in a first defined plane, and the user may step on the foot pedal 128 to relay to the computing system 102 that the tool axis 207 needs to be maintained in a second defined plane.

Surgical Planning and Execution for a Total Knee Arthroplasty (TKA) Application

Figure 3:
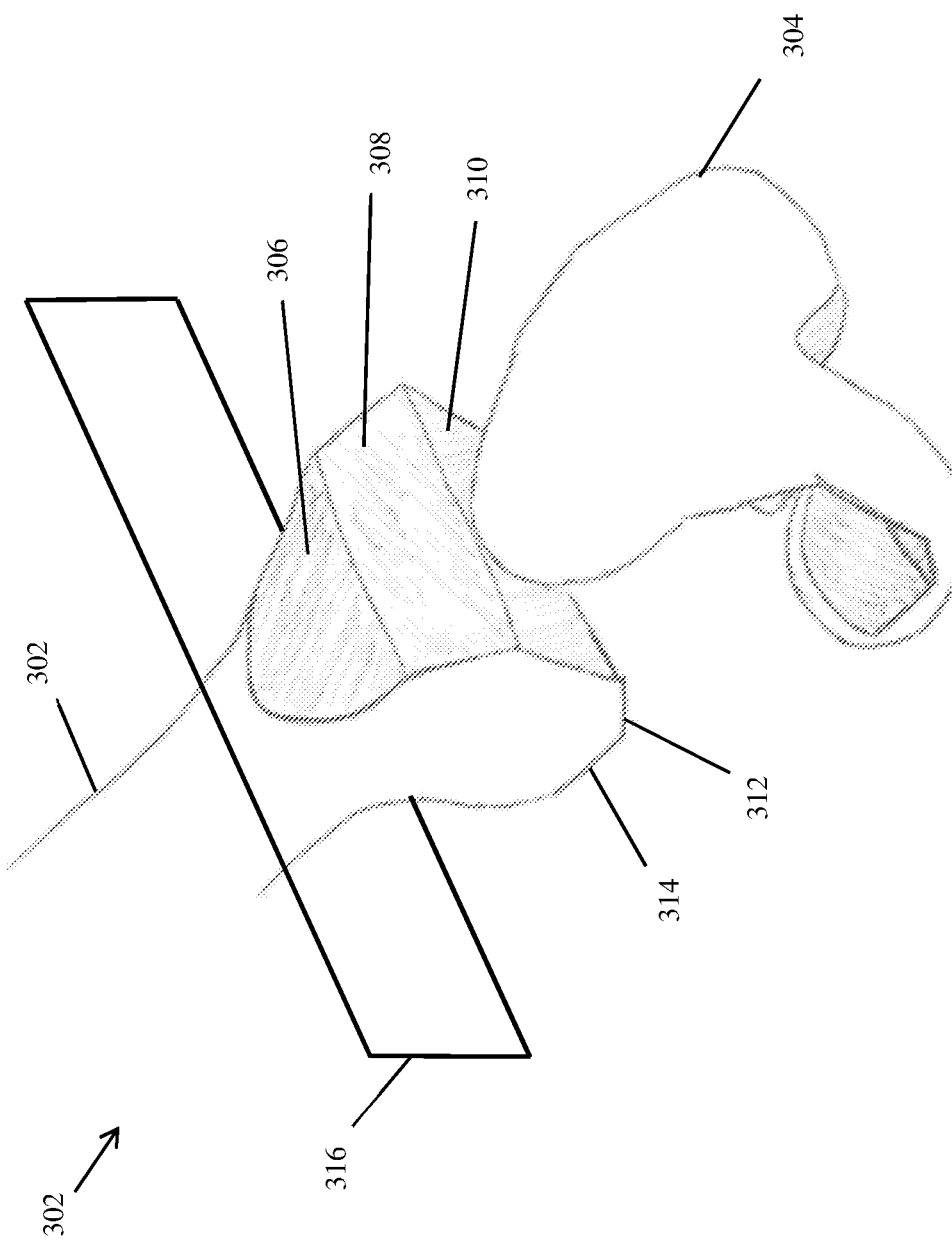
FIG. 3 illustrates a virtual plane defined relative to a planned cut plane on a three dimensional model of a bone in accordance with embodiments of the invention.

The surgical plan is created, either pre-operatively or intra-operatively, by a user using planning software. The planning software may be used to a generate three-dimensional (3-D) models of the patient's bony anatomy from a computed tomography (CT), magnetic resonance imaging (MRI), x-ray, ultrasound image data set, or from a set of points collected on the bone intra-operatively. A set of 3-D computer aided design (CAD) models of the manufacturer's prosthesis are pre-loaded in the software that allows the user to place the components of a desired prosthesis to the 3-D model of the boney anatomy to designate the best fit, position and orientation of the implant to the bone. For example, with reference to FIG. 3, a 3-D model of the patient's distal femur 302 and a 3-D model of the femoral prosthesis 304 are shown. The final placement of the femoral prosthesis model 304 on the bone model 302 defines the bone cut planes (shaded regions of the bone model 302) where the bone is cut intra-operatively to receive the prosthesis as desired. In TKA, the planned cut planes generally include the anterior cut plane 306, anterior chamfer cut plane 308, the distal cut plane 310, the posterior chamfer cut plane 312, the posterior cut plane 314 and the tibial cut plane (not shown).

The surgical plan contains the 3-D model of the patient's operative bone combined with the location of one or more virtual planes 316. The location of the virtual plane(s) 316 is defined by the planning software using the position and orientation (POSE) of one or more planned cut planes and one or more dimensions of a cutting guide or alignment guide. Ultimately, the location of the virtual plane(s) 316 is defined to aid in the placement of a cutting guide such that one or more guide slots of the cutting guide are in the correct POSE to accurately guide a saw in creating the bone cuts. Embodiments of the various inventive cutting guides, alignment guides, defining of the virtual planes, and use of the bone pins are further described in detail below.

In general, embodiments of the inventive cutting guides and alignment guides disclosed herein may be made of a rigid or semi-rigid material, such as stainless steel, aluminum, titanium, polyetheretherketone (PEEK), polyphenylsulfone, acrylonitrile butadiene styrene (ABS), and the like. Embodiments of the cutting guides and alignment guides may be manufactured using appropriate machining tools known in the art.

Distal Cutting Guide, Alignment Guide and N-in-1 Cutting Block

Figure 4B:
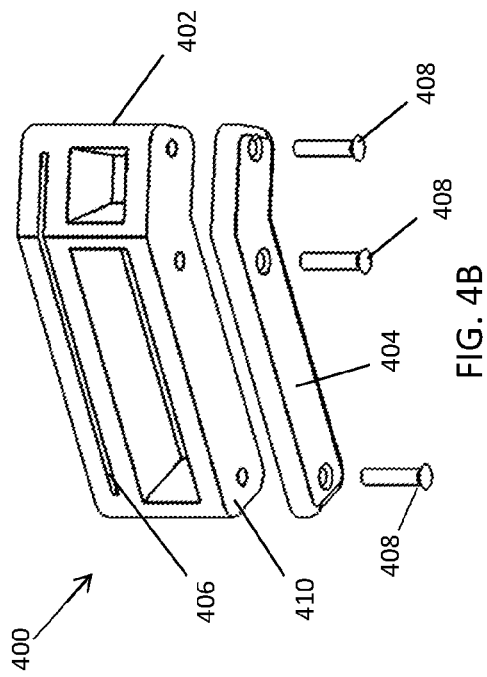
FIGS. 4A and 4B depicts a universal distal cutting guide for creating a distal cut on a bone in accordance with embodiments of the invention as a front view (FIG. 4A) and perspective view (FIG. 4B)
Figure 4D:
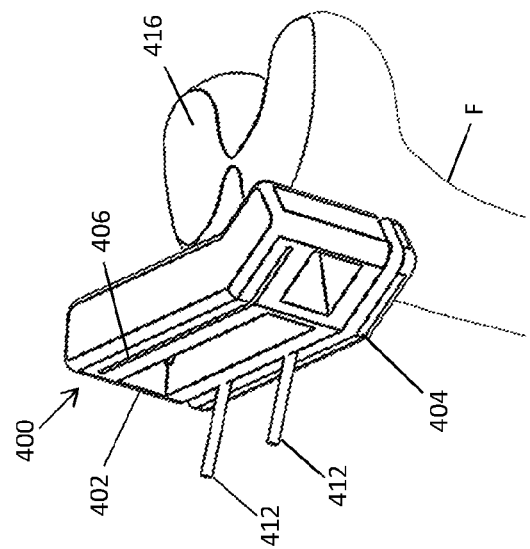
FIG. 4D depicts the universal distal cutting guide of FIGS. 4A and 4B secured to bone using the bone pins of FIG. 4C.
Figure 4A:
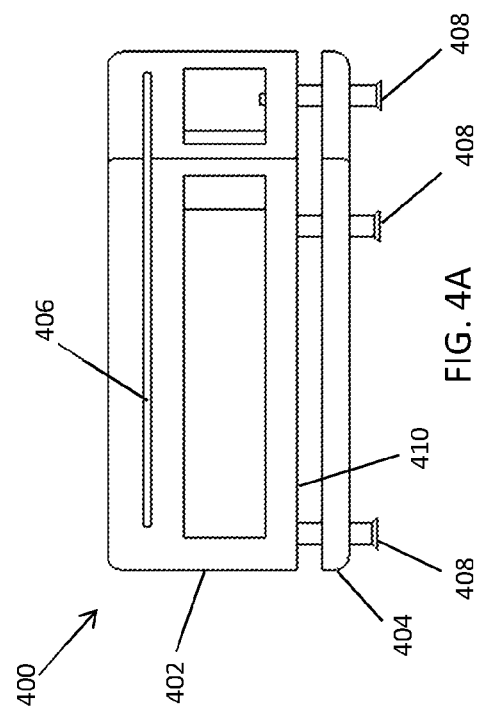
Figure 4C:
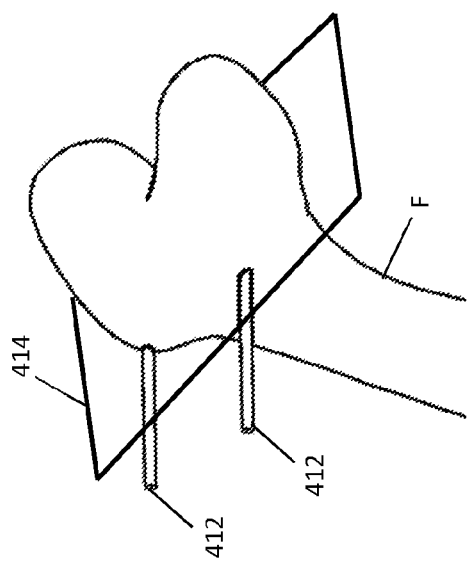
FIG. 4C depicts bone pins positioned in the context of a bone.

A particular inventive embodiment of a cutting guide to accurately create the planned distal cut 310 is the universal distal cutting guide 400 as depicted in FIG. 4A and FIG. 4B. The distal cutting guide 400 includes a guide portion 402 and an attachment portion 404. The guide portion 402 includes a guide slot 406 and a bottom surface 410. The guide slot 406 is for guiding a surgical saw in creating the distal cut 310 on the femur. The bottom surface 410 abuts against one or more bone pins 412 that are placed on the bone. The attachment portion 404 and the guide portion 402 clamp to the bone pins 412 using fasteners 408 as shown in FIG. 4B and FIG. 4D.

A surgical system is used to place the longitudinal axis of the bone pins 412 on a virtual pin plane 414. In a particular embodiment, the 2-DOF surgical system 100 is used, wherein the tool 206 of the surgical device 104 is a drill bit rotated by the drill 205. As the user manipulates the surgical device 104, the computing system supplies actuation commands to the actuators to align the tool axis 207 with the pin plane 414.

The virtual pin plane 414 is defined in the surgical plan by the planning software using the POSE of the planned distal cut plane 310, and the distance between the guide slot 406 and the bottom surface 410 of the guide portion 402. The planning software may also use the known width of the bone pins 412. For example, the pin plane 414 can be defined by proximally translating the planned distal cut plane 310 by the distance between the guide slot 406 and the bottom surface 410 of the distal cutting guide 400. The software may further proximally translate the planned distal cut plane 310 by an additional half width of the pins 412. Therefore, when the cutting guide 400 is clamped to the bone pins 412, the guide slot 406 is aligned with the planned distal cut plane 310.

The user or the computing system 102 may activate the drill when properly aligned with the pin plane 414 to drill pilot holes for the pins 412. The pins 412 are then drilled into the pilot holes using a standard drill. In a specific embodiment, the tool 206 is the pin 412, wherein the pin 412 is attached to the drill 205 of the surgical device 104 and drilled directly into the bone on the pin plane 414. At least two bone pins 412 may be drilled on the pin plane 414 to constrain the distal cutting guide 400 in the proper position and orientation when clamped to the pins 412 however three or more bone pins 412 can be used for further stability.

There are multiple advantages to using the 2-DOF surgical system 100 to accurately place the bone pins 412. For one, the surgical device 104 is actuating in real-time, therefore the user is actively guided to the POSE of the pin plane 412. In addition, the correct position and orientation of the bone pins 412 is accurately maintained regardless of the surgeon's placement of the hand-held portion 204 of the 2-DOF surgical system 100.

One main advantage of the cutting guide 400 is its universality because the cutting guide 400 may be used for any type of implant and any type of patient. This is particularly advantageous, because the universal distal cutting guide 400 can be sterilized and re-used for multiple surgeries, greatly reducing the cost of TKA, which otherwise requires either patient specific cutting guides or implant specific cutting guides for each surgery.

The advantageous part of using pin planes, rather than defining a specific location for the bone pins 412, is the user can place the longitudinal axes of the pins in any arbitrary orientation and position on the plane 414 and still attach the cutting guide 400 such that the guide slot 406 is accurately aligned with the planned distal cut plane 310. This greatly reduces the operational time of the procedure. In addition, the user can avoid any particular landmarks coincident with the virtual plane if so desired.

After the cutting guide 400 is assembled on the bone pins 412, the user can saw the distal cut 416 on the femur F by guiding a surgical saw through the guide slot 406. Subsequently, the bone pins 412 and cutting guide 400 are removed from the bone to create the remaining bone cuts.

Figure 5B:
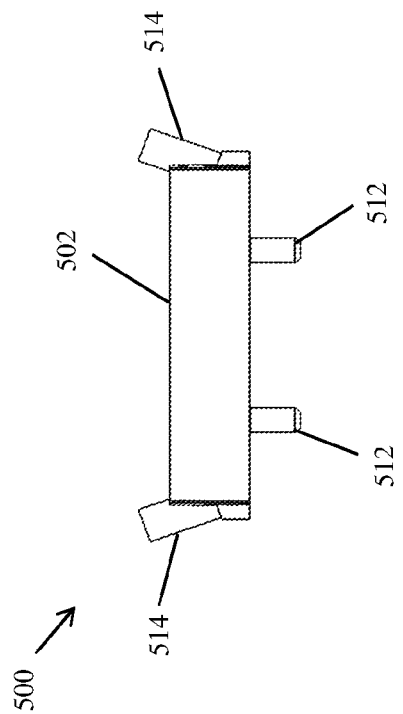
FIGS. 5A-5D depicts a 4-in-1 cutting block for creating multiple cut planes on a bone in accordance with embodiments of the invention in perspective view (FIG. 5A), side view (FIG. 5B), bottom view (FIG. 5C), and top view (FIG. 5D)
Figure 5D:
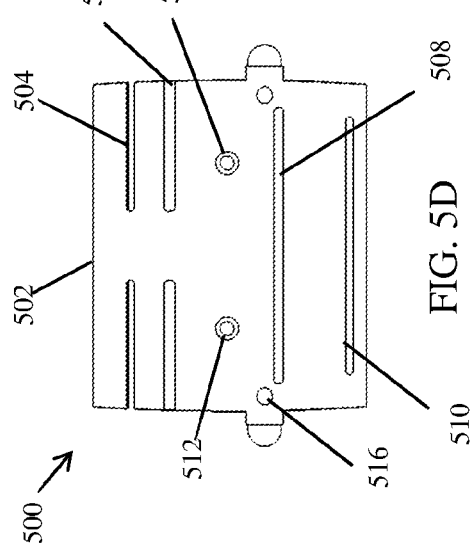
Figure 5A:
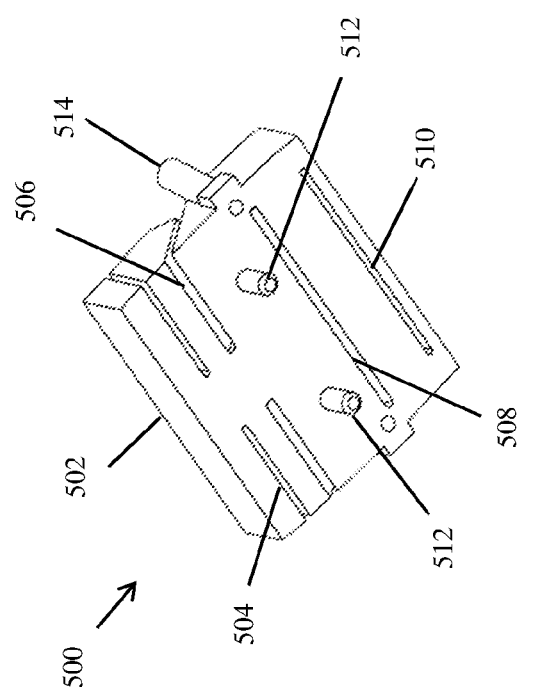
Figure 5C:
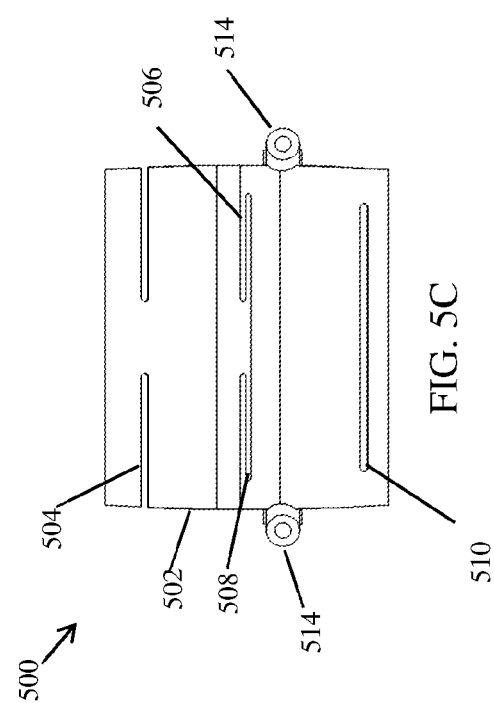

In a particular embodiment, with respect to FIGS. 5A-5D, a prior art 4-in-1 cutting block 500 is used to create the remaining bone cuts. FIG. 5A is a perspective view of the 4-in-1 cutting block, FIG. 5B is a side elevation view thereof, FIG. 5C is a top plan view thereof, and FIG. 5D is a bottom plan view thereof. The 4-in-1 cutting block 500 may be made of materials similar to that of the distal cutting guide 400. The 4-in-1 cutting block 500 is manufactured to include a body 502, a posterior guide slot 504, a posterior chamfer guide slot 506, an anterior chamfer guide slot 508, and an anterior guide slot 510. The cutting block 500 also includes two pegs 512 to fit into pilot holes to be drilled on the distal cut plane 416, and two pin securing guides 514 to receive pins 412' to secure the cutting block 500 to the femur F. Although a 4-in-1 cutting block 500 is described herein, it should be appreciated that any N-in-1 cutting block for creating additional cut-planes on the bone may be aligned and assembled on the bone using the embodiments described herein. An N-in-1 cutting block can account for femoral prostheses having greater than 5 planar contact surfaces (for reference and clarity, the femoral prosthesis 304 shown in FIG. 3 has 5 planar contact surfaces including the posterior contact surface 318 that mates with the posterior cut plane 314).

Figure 6B:
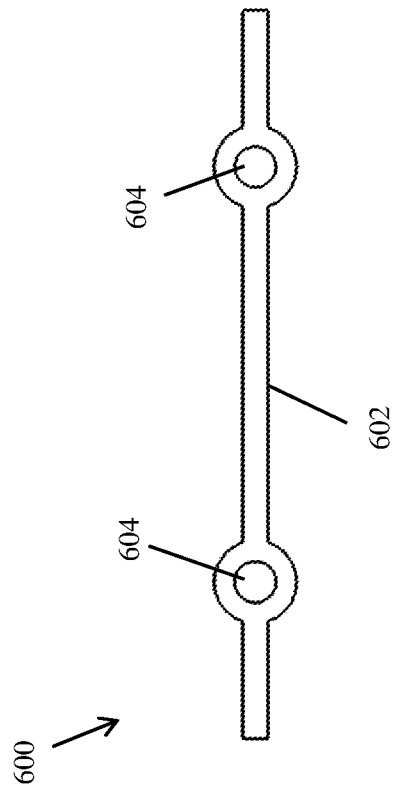
FIGS. 6A and 6B depicts a planar alignment guide for aligning a N-in-1 block on a bone in accordance with embodiments of the invention in perspective view (FIG. 6A), and top view (FIG. 6B)
Figure 6A:
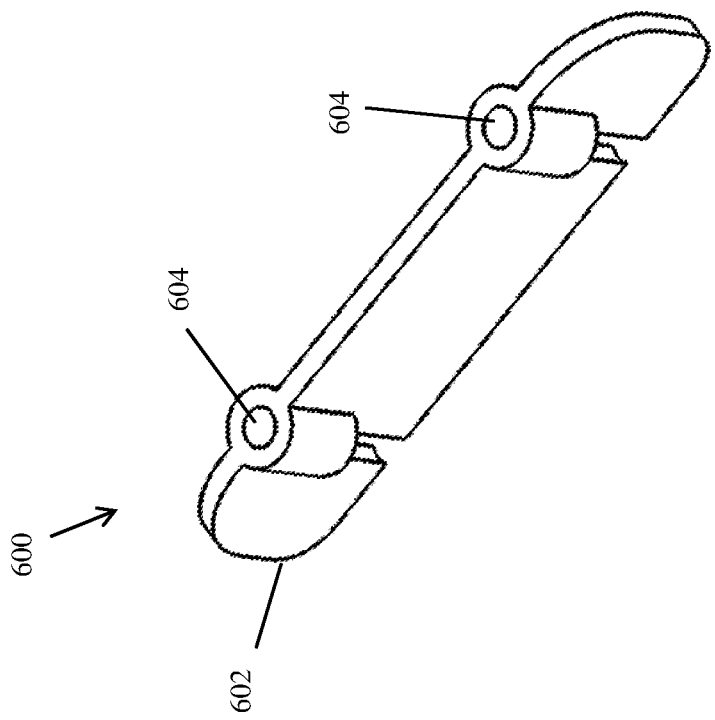
Figure 8A:
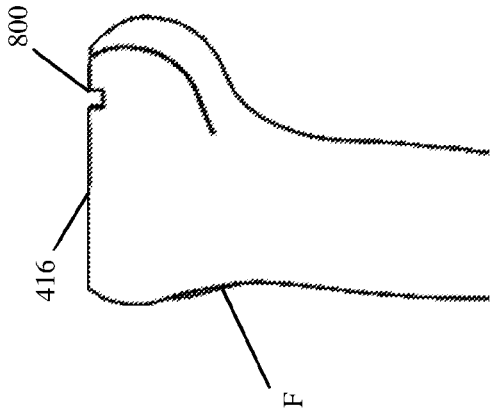
FIGS. 8A-8D depicts a channel created on the distal surface of the femur in perspective view (FIG. 8A) and in side view (FIG. 8B) for receiving an alignment guide in accordance with embodiments of the invention with the alignment guide depicted in the channel in perspective view (FIG. 8C) and top view (FIG. 8D)
Figure 8B:
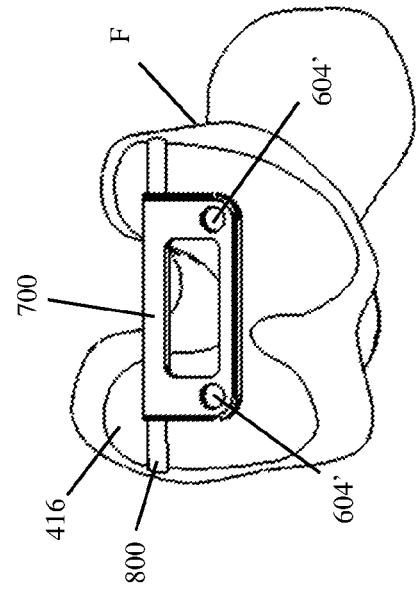

The 4-in-1 cutting block 500 may be aligned on the bone using an alignment guide. A particular embodiment of the alignment guide is a planar alignment guide 600 as shown in FIG. 6A and FIG. 6B. FIG. 6A is a perspective view of the planar alignment guide 600, and FIG. 6B is a top plan view of thereof. The planar alignment guide 600 includes a body 602, and two holes 604 integrated with the body 602. The body 602 includes a bottom portion 606 adapted to fit in a channel 800 (shown in FIG. 8A) to be milled on the distal cut plane 416. The distance between the centers of the holes 604 correspond to the distance between the centers of the pegs 512 of the 4-in-1 block 500.

Figure 7B:
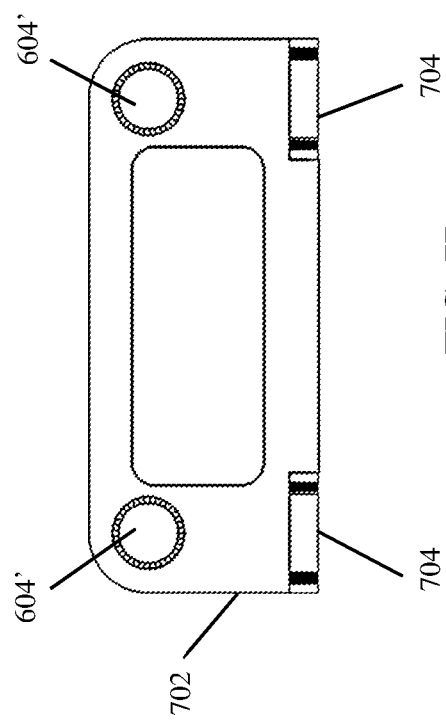
FIGS. 7A and 7B depicts an offset alignment guide for aligning a N-in-1 block on a bone in accordance with embodiments of the invention in perspective view (FIG. 7A), and top view (FIG. 7B)
Figure 7A:
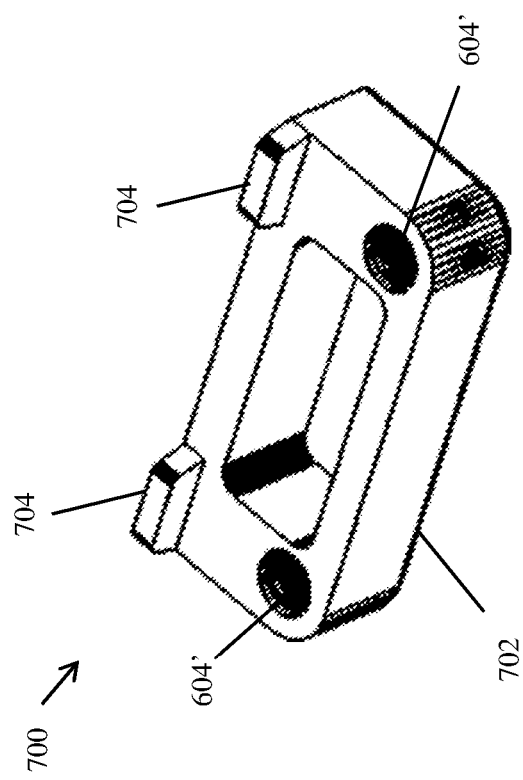

With reference to FIGS. 7A and 7B, a particular embodiment of the alignment guide is an offset alignment guide 700. FIG. 7A is a perspective view of the alignment guide 700, and FIG. 7B is a bottom plan view thereof. The alignment guide 700 includes a body 702, at least one ridge 704 at the edge and extending from the body 702, and two holes 604' bored through the body 702, where the two holes 604' are located a known distance from the ridge 604. The distance between the centers of the two holes 604' correspond to the distance between the pegs 512 of the 4-in-1 cutting block 500. The at least one ridge 704 is adapted to fit in a channel 800 (shown in FIG. 8A) to be milled on the distal cut plane 416.

The location of the pegs 512 on the distal cut plane 310 is determined based on the planned size and location of the prosthesis such that the guide slots of the 4-in-1 cutting block 500 align with the remaining bone cut planes. The planning software can define a virtual channel plane in the surgical plan, in which a channel 800 will be milled to receive the alignment guide (600, 700). In a particular embodiment, the channel plane is defined by a plane that is perpendicular to the distal cut plane and aligned with the medial-lateral direction of the prosthesis. In another embodiment, the channel plane is defined based on the POSE of the planned anterior cut plane 306 or posterior cut plane 314, and the location of the pegs required to align the guide slots for the remaining bone cuts. For example, if the planar alignment guide 600 is used, the planning software can define a virtual channel plane by anteriorly translating the planned posterior cut plane 314 to the location of the center of the pegs 512 of the 4-in-1 cutting block 500. If the offset alignment guide 700 is used, then, the virtual channel plane is defined by anteriorly translating the planned posterior cut plane 314 to the location of the pegs 512, and then posteriorly/anteriorly translating the planned plane by the known distance between the center of the holes 604' and the ridge 704.

Figure 8C:
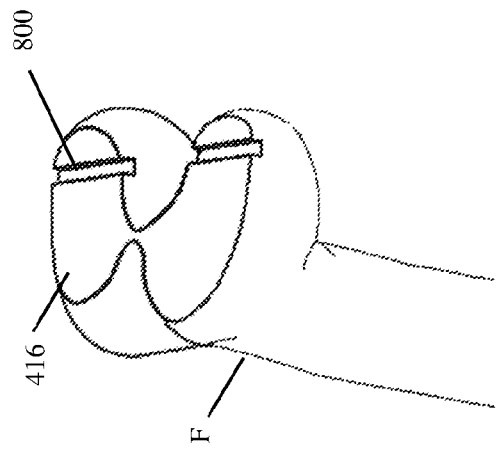
Figure 8D:
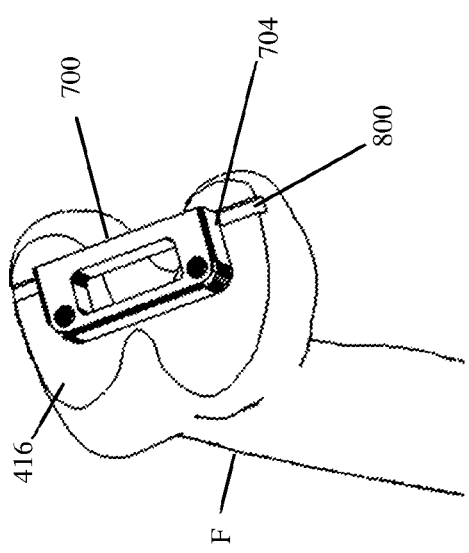

The virtual channel plane defined in the surgical plan is used to create a channel 800 on the distal cut plane 310 of the femur F with a surgical system as shown in FIGS. 8A-8D. In a particular embodiment, the 2-DOF surgical system 100 is used wherein the tool 206 of the surgical device 104 is actuated such that the tool axis 207 remains substantially coincident with the channel plane. To mill the channel 800, the tool 206 is a bone cutting tool such as an end mill, burr or a rotary cutter. The tool 206 may further include a sleeve to prevent the tool 206 from cutting the channel 800 too deep. After the channel 800 is milled, the alignment guide is placed in the channel, whereby the holes 604' are aligned with the position for the pegs 512 of the 4-in-1 cutting block 500. When using the planar alignment guide 600, the bottom portion 606 of the body 602 fits directly in the channel. When using the offset alignment guide 700, the ridge 704 fits directly into the channel 800 as shown in FIGS. 8C and 8D. In both cases, a standard drill is then used to drill pilot holes for the pegs 512 by drilling through the holes 604' of the alignment guide.

After the holes for the pegs 512 have been drilled, the alignment guide is removed from the femur F. The 4-in-1 block 500 is attached to the femur F via the pegs 512. The remaining four bone cuts on the femur F are created using a surgical saw guided by the guide slots of the 4-in-1 cutting block 500. The 4-in-1 block 500 is then removed, and the femoral prosthesis can be fixed to the femur F in a conventional manner.

A particular advantage in using the offset alignment guide 700 as opposed to the planar alignment guide 600, is the created channel 800 to receive the ridge 704 can be removed with one of the four planar cuts, depending on the distance between the ridge 704 and the holes 604'. In general, the use of the channel plane with an alignment guide (600, 700) is advantageous because position of the cutting block 500 in the medial-lateral direction does not need to be precise on the distal cut 416 as long as the guide slots of the 4-in-1 cutting block 500 span enough of the bone to create the remaining bone cuts. Additionally, by using a surgical system, the channel can be quickly and accurately created. In combination, all of these are highly advantageous over the traditional cutting alignment guides because there is no need to reference a monitor if passive navigation was otherwise used, there is no need to locate multiple anatomical landmarks to drill the holes for the pegs of a 4-in-1 block, and the overall surgical time is reduced.

Distal Cutting Guide with Alignment Guide

In a particular embodiment of the cutting guide, a distal cutting and alignment guide 900 is illustrated in FIG. 9A and FIG. 9B. A front perspective view of the distal cutting guide 900 is shown in FIG. 9A, and a rear perspective view thereof is shown in FIG. 9B. The distal cutting and alignment guide 900 includes a guide portion 902 and an attachment portion 904. The guide portion 902 may be in the shape of an inverted "L", with a distal guide slot 906 and a pair of holes 908 bored through. The distance between the centers of the two holes 908 correspond to the distance between the pegs 512 of the 4-in-1 block 500. The guide portion 902 also includes an abutment face 912 adapted to abut against alignment pins 914. The attachment portion 904 attaches to the guide portion 902 with fasteners 910 to clamp bone pins 912 to the distal cutting and alignment guide 900.

The planning software defines two virtual planes to accurately place the cutting and alignment guide 900 to the femur F. A first pin plane is defined such that the guide slot 906 aligns with the planned distal cut plane 310 when the cutting guide 900 is assembled to the bone pins 912. A second pin plane is defined such that when the face 912 abuts against the alignment pins 914 second pin plane, the holes 908 align with the POSE for the pegs 512 of the 4-in-1 cutting block 500. For example, in FIG. 9C, the first pin plane is defined for the bone pins 912 and the second pin plane is defined for the alignment pins 914. The second pin plane is defined in the planning software as follows: 1) a plane is defined perpendicular to the planned distal cut plane 310 and parallel with the planned position for the pegs 512, and 2) that plane is then posteriorly translated by the distance between the centers of the holes 908 and the face 912 of the distal cutting and alignment guide 900. Therefore, when the face 912 abuts against the alignment pins 914, the holes 908 are accurately aligned in the anterior/posterior direction and internal-external rotation.

The bone pins 912 and alignment pins 914 are accurately placed on the first and second pin planes using a surgical system as described above. The cutting guide 900 is then assembled to the femur F, wherein the face 912 abuts against the alignment pins 914 as shown in FIG. 9D. Before the surgeon creates the distal cut 416, two pilot holes are drilled through the holes 908. The alignment pins 914 are removed and the distal cut 416 is made by guiding a surgical saw through the guide slot 906. The cutting guide 900 is removed from the femur F, and the 4-in-1 guide block can be directly assembled in the pilot holes to aid in creating the remaining cuts.

Slot Alignment Guide

Figure 10A:
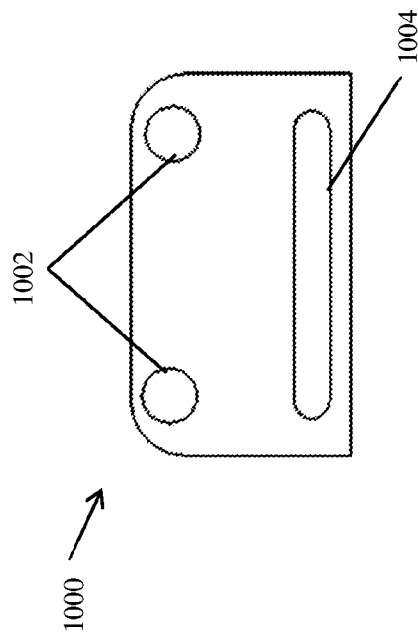
FIGS. 10A and 10B depict a slotted alignment guide for aligning a N-in-1 cutting block in accordance with embodiments of the invention in perspective view (FIG. 10A), and top view (FIG. 10B)
Figure 10B:
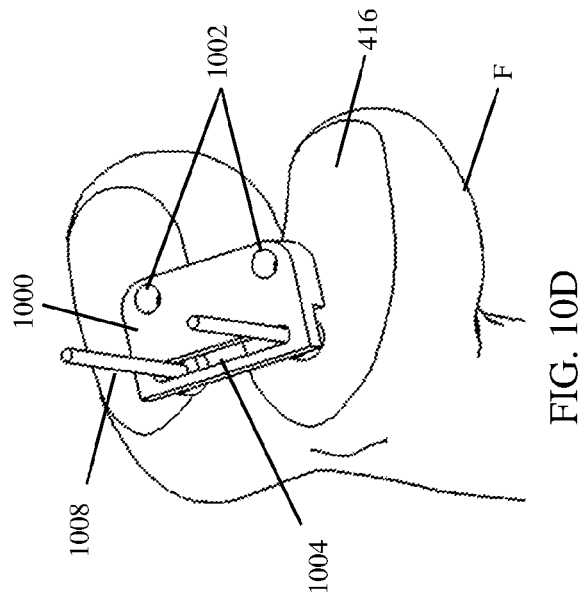

In a particular embodiment of the alignment guide, a slot alignment guide 1000 is shown in FIG. 10A and FIG. 10B. FIG. 10A is a perspective view of the slot alignment guide 1000, and FIG. 6B is a top plan view thereof. The slot alignment guide 1000 includes two holes 1002, and a pin receiving slot 1004. The slot alignment guide 1000 may further include a lip 1006. The distance between the centers of the two holes 1002 correspond to the distance between the pegs 512 of the 4-in-1 block 500. The pin receiving slot 1004 is of sufficient width to be received on the bone pins 1008. The distance between the center of the slot 1004 and the holes 1002 are known to define a virtual pin plane for the bone pins 1008.

Figure 10C:
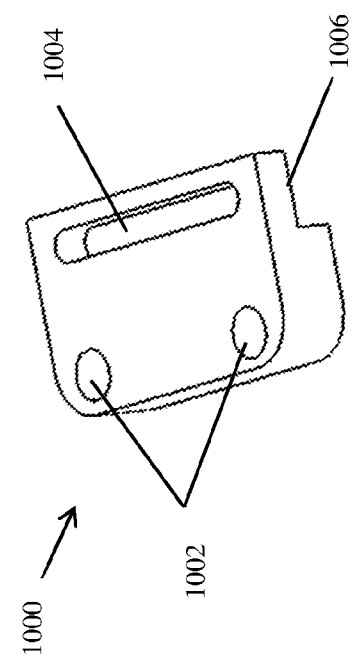
FIG. 10C depicts bone pins positioned in the context of a bone.
Figure 10D:
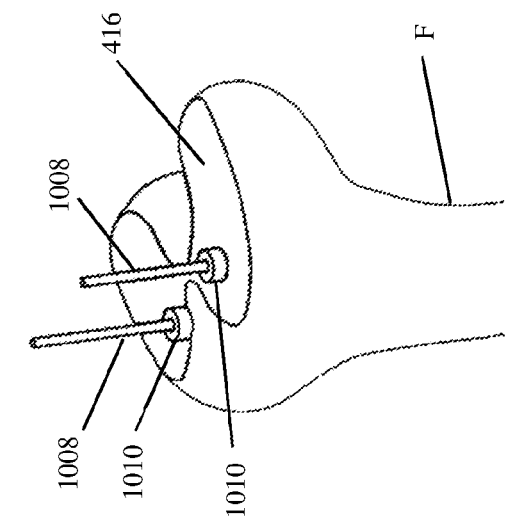
FIG. 10D depicts the universal cutting guide with a N-in-1 cutting block alignment guide of FIGS. 10A and 10B secured to bone using the bone pins of FIG. 10C.

The slot alignment guide 1000 may be used if the cancellous bone on the distal surface 416 of the femur F is particularly soft, weak, or more flexible. In these cases, the planar alignment guide 600 or the offset alignment guide 700 in the channel 800 may become misaligned due to the flexible nature of this cancellous bone. Therefore, bone pins 1008 may be inserted on the channel plane as defined above. The bone pins 1008 are aligned and inserted on the channel plane using the methods previously described as shown in FIG. 10C. A ring 1010 such as a washer or spacer may be placed on the bone pins 1008 to further protect the distal surface 416 of the femur F. The pin receiving slot 1004 of the slot alignment guide 1000 is placed on the bone pins 1000. The lip 1006 may interact with the ring 1010 such that the alignment guide 1000 lies flat on the distal surface 416 of the femur F. A user may then drill pilot holes through the holes 1002 using a standard drill. The alignment guide 1000 and the bone pins 1008 are removed from the femur F and the pegs 512 of the 4-in-1 guide block 500 is assembled to the pilot holes to aid in creating the remaining bone cuts.

It should be appreciated that the 4-in-1 block may have other features, other than the pegs 512, to interact and attach with the distal cut surface 416 of the femur F. The pegs 512 may instead be a body extruding from the bottom surface of the 4-in-1 block 500 and adapted to fit in a corresponding shape created on the distal cut surface 416. The extruding body may have a variety of shapes including an extruded rectangle, triangle, the shapes manufactured for a keel of a tibial base plate implant, and any other extruding body/bodies. Therefore, the alignment guides described herein may have the same corresponding shape, instead of the holes (604, 604', and 908), to guide a user in creating that shape on the distal cut surface 416 so the 4-in-1 block can be accurately placed thereon.

Clamp Alignment Guide

With reference to FIGS. 16A-17C, a clamp alignment guide (1600, 1700) is used to aid in the alignment of an N-in-1 cutting block on the femur. The clamp alignment guides (1600, 1700) are configured to clamp onto their own set of pins in a POSE that permits a user to accurately create the pilot holes for the cutting block pegs 512. In a particular embodiment, with reference to FIGS. 16A-16E, a referencing clamp alignment guide 1600 and the use thereof is shown. The referencing clamp alignment guide 1600 includes a guide portion 1602 and a clamping portion 1604. The guide portion 1602 has a pair of referencing feet 1606 that reference a top surface 409 of the universal distal cutting guide 400', and two or more holes 1608 spaced a distance apart corresponding to the distance between the pegs 512 of a cutting block.

In general, the virtual pin plane for the clamp alignment guides (1600, 1700) is defined by: 1) defining a plane perpendicular to the planned distal cut plane 310 and parallel with the planned position for the pegs 512; 2) posteriorly translating that plane by the known distance between the centers of the holes 1608 and a bottom surface 1609 of the alignment portion 1602; and 3) further posteriorly translating that plane by an additional half-width of the pins 1610.

Figure 16A:
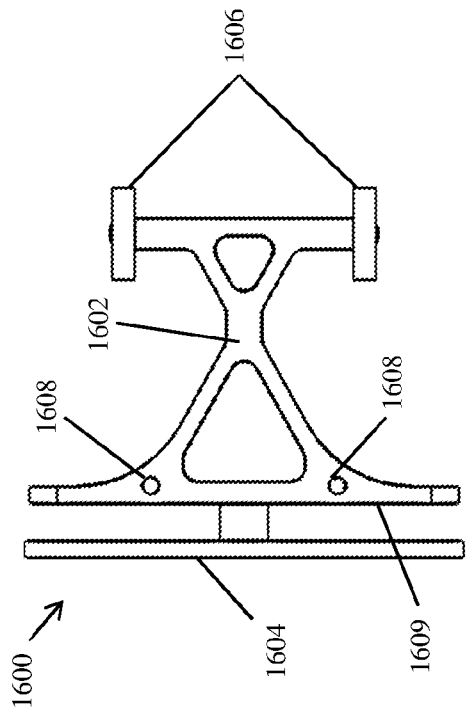
FIGS. 16A and 16B depicts a referencing clamp alignment guide for creating pilot holes on the bone to align a N-in-1 cutting block in accordance with embodiments of the invention.
Figure 16B:
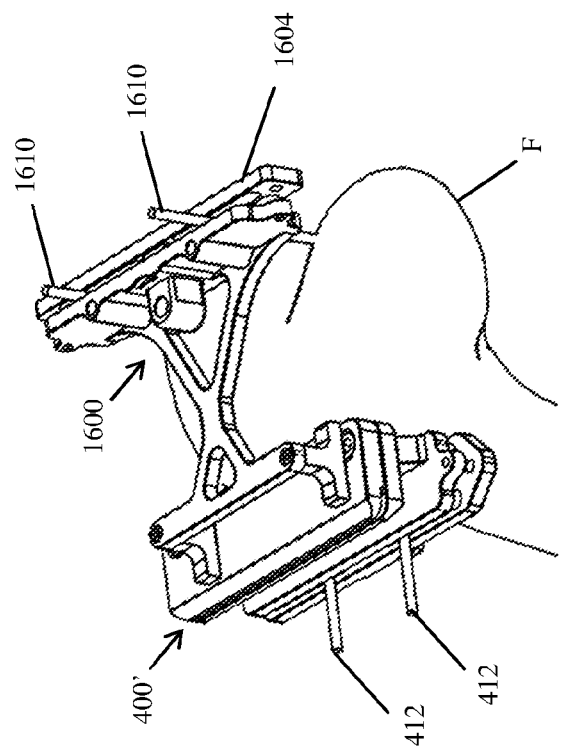
Figure 16C:
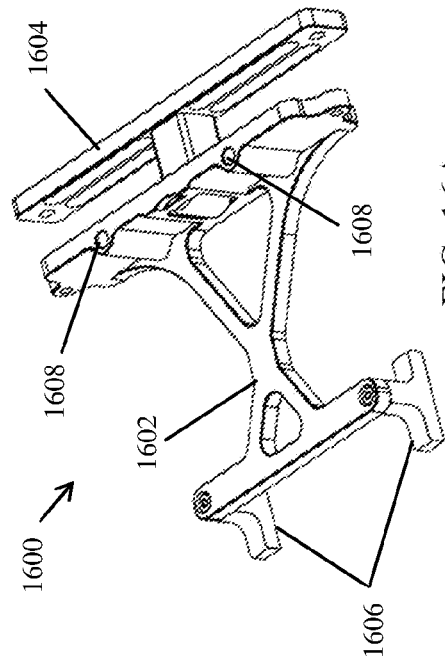
FIGS. 16C and 16D illustrates the use of the referencing clamp alignment guide in accordance with embodiments of the invention.
Figure 16D:
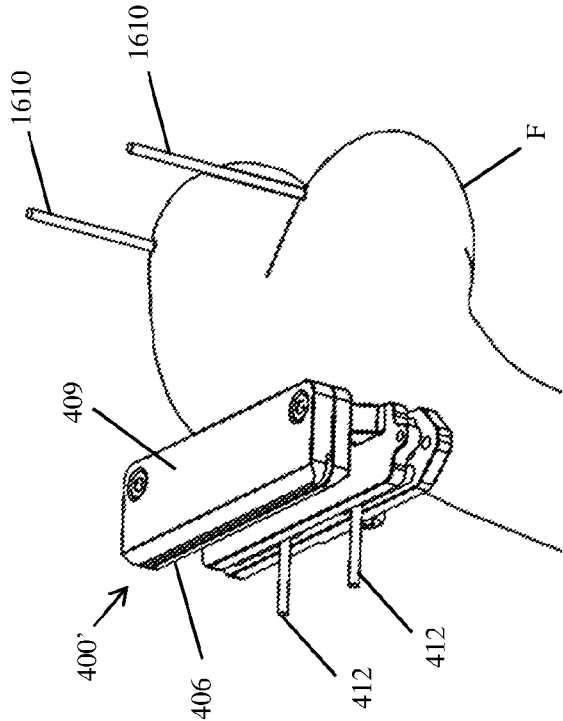

Use of the reference clamp alignment guide 1600 is shown with respect to FIGS. 16C and 16D. A universal cut guide 400' is first assembled on the femur F as described above. The pins 1610 are positioned on the virtual pin plane using a surgical system, such as the 2-DOF surgical system 100. The clamp guide 1600 is assembled on the pins 1610 with the feet 1606 referencing the top surface 409 of the universal cut guide 400'. The user then drills the pilot holes for the cutting block pegs 512 using the holes 1608 as a guide. After which, the clamp alignment guide 1600 and pins 1610 are removed from the bone and the user creates the distal cut via the guide slot 406. Subsequently, the distal cut guide 400' and distal pins 412 are removed from the bone, the cutting block pegs 512 are inserted in the pilot holes, and the remaining cut planes are created on the femur.

There is one issue a user may encounter when using the clamp alignment guides (1600, 1700). The drill and drill bit for creating the N-in-1 pilot holes need to have sufficient clearance so as to not interfere with the placement of the pins 1610, while also permitting the drill bit to traverse all of the bone distal to the distal cut plane and create a hole beyond the distal cut plane that is deep enough to fully receive the cutting block pegs 512. In a particular embodiment, with reference to FIG. 16E, this problem is solved using a stepped diameter drill bit 1617. FIG. 16E depicts the distal cut guide 400' and reference clamp guide 1600 assembled on the bone, and a drill 1618 driving a stepped diameter drill bit 1617 through the guide holes 1608. Because the exact distance between the planned distal cut plane 1612 and the top of the guide 1614 is known (this is geometrically known because the distance from i) the guide slot 406 and the distal guide's top surface 409 is known, and ii) the distance from the bottom of the referencing feet 1606 stabilized on the top surface 409, to the top of the guide 1614 is also known, therefore i+ii=the distance between the top of the guide 1614 and the planned cut plane 1612), a drill bit 1617 having a stepped diameter can simultaneously clear the length of the pins 1610 and also set the engagement in the bone beyond the distal cut plane 1612 so the user does not have to determine how deep to drill. Here the drill bit 1617 has a distal portion 1619 having a diameter less than a proximal portion 1620. The distal portion 1619 has a diameter that fits through the guide holes 1608 and large enough to create a hole for receiving the cutting block pegs 512. The distal portion 1619 has a length capable of traversing the bone distal of the distal cut plane 1619 and extend beyond the distal cut plane 1612 enough to create a pilot hole deep enough to fully receive the pegs 512. The proximal portion 1620 has a diameter larger than the diameter of the guide holes 1608 and a length that ensures the bulky drill 1618 does not interfere with pins 1610. In another embodiment, to solve this clearance issue, the drill 1618 is tracked by a tracking system and a monitor provides visual feedback to the user. When the tip of the drill extends beyond a certain depth (e.g. breaks the planned distal cut plane 1612), the monitor displays this information and/or provides depth information.

Figures 17A, 17B, 17C:
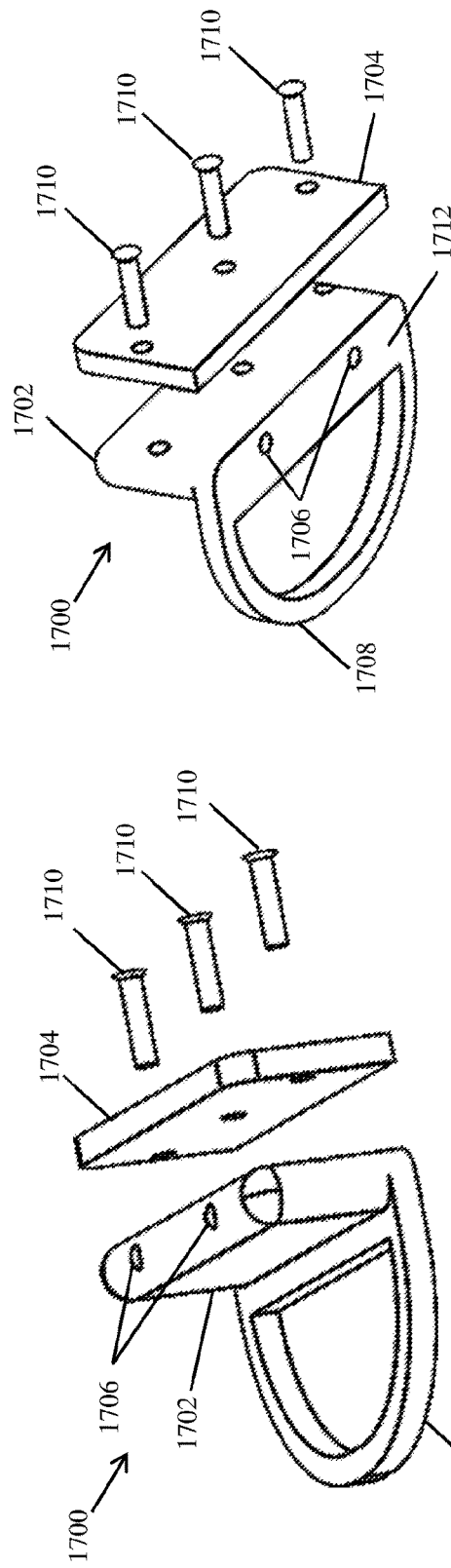
FIGS. 17A and 17B depict a plane clamp alignment guide for creating pilot holes on a distal cut surface to align a N-in-1 cutting block in accordance with embodiments of the invention.
FIG. 17C illustrates the use of the plane alignment guide in accordance with embodiments of the invention.

In a specific embodiment, with reference to FIGS. 17A-17C, a plane clamp alignment guide 1700 is used to aid in the creation of the pilot holes to receive the cutting block pegs 512. The plane alignment guide 1700 is placed directly on the distal cut plane 416 and includes a guide portion 1702 and a clamping portion 1704. The guide portion 1700 includes two or more holes 1706 similar to the reference alignment guide 1600. The guide 1700 may further include a projection 1708 to increase the contact surface area between the guide 1700 and the distal cut surface 416 to increase the stability of the guide on the distal surface 416. Accordingly, the bottom surface 1712 of the plane alignment guide 1700 is flat to mate with the planar distal cut surface 416. Fasteners 1710 or a clamping mechanism allows the plane guide 1700 to assemble to the pins 1714 inserted on the bone.

The procedure for using the plane alignment guide 1700 is as follows. The user first creates the distal cut using a universal distal cutting guide 400. The user then inserts pins 1714 on a virtual pin plane, where the virtual pin plane is defined as described above for the clamp alignment guides (1600, 1700). The pins 1714 are inserted directly on the distal cut surface 416. The plane alignment guide 1700 is then clamped to the pins 1714 where the bottom surface 1712 of the guide 1700 lies flush with the cut surface 416. The user drills the pilot holes for the pegs 512 using the holes 1706 as a guide. Subsequently, the pins 1714 and the plane alignment guide 1700 are removed, the pegs 512 of an N-in-1 cutting block are placed in the pilot holes, and the remaining cut planes are created. The clearance issue described above for the reference alignment guide 1600 can be readily solved in a similar manner for the plane alignment guide 1700.

5-DOF Chamfer Guide

Figure 11B:
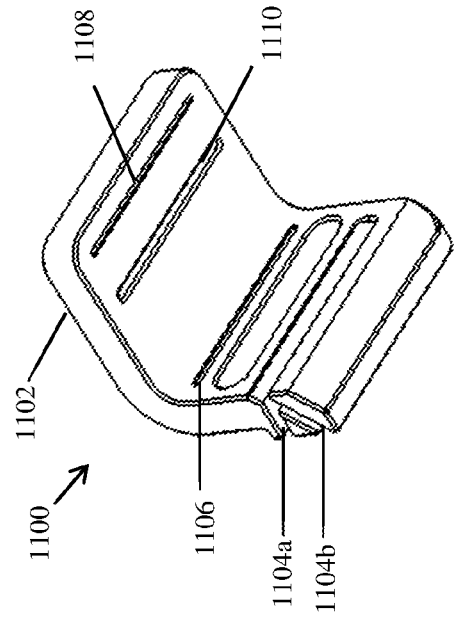
FIGS. 11A-11E depict a 5-degree-of-freedom chamfer cutting guide for creating multiple planar bone cuts in accordance with embodiments of the invention.
Figure 11A:
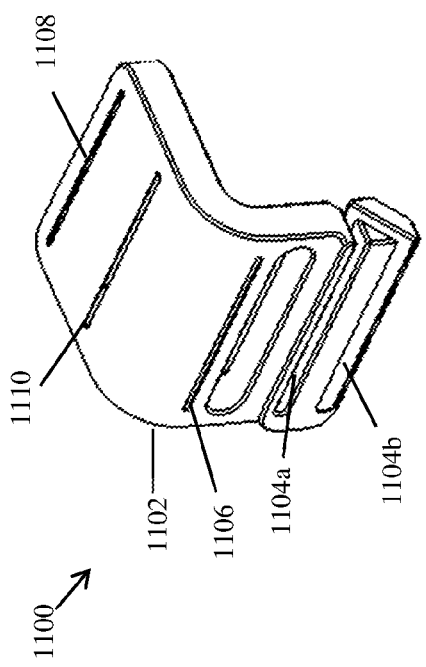
Figure 11E:
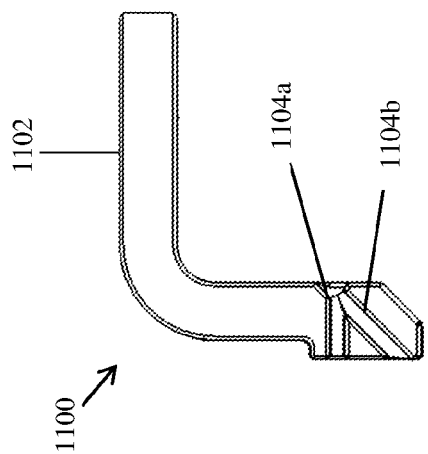
Figure 11D:
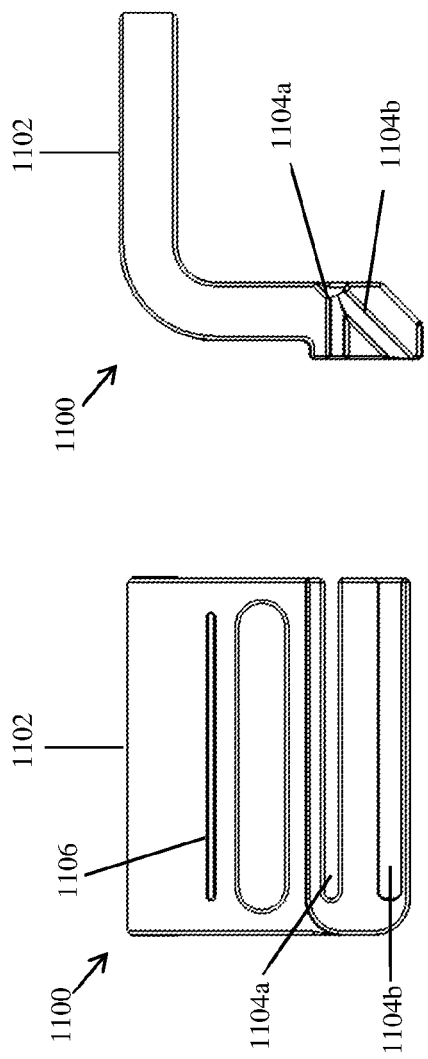
Figure 11C:
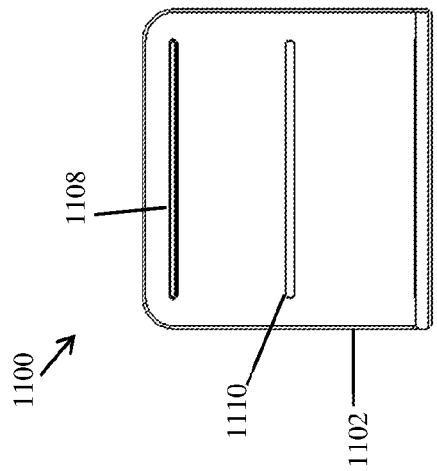

In a specific embodiment of the cutting guide, a 5-DOF chamfer cutting guide 1100 is shown in FIGS. 11A-11E. FIG. 11A is a perspective view of the top of the chamfer cutting guide 1100, FIG. 11B is a perspective view of the bottom thereof, FIG. 11C is a top plan view, FIG. 11D is a front elevation view, and FIG. 11E is a side elevation view. The chamfer cutting guide 1100 includes a guide body 1102 in the shape of an inverted "L". The guide body 1102 includes a first attachment slot 1104a, a second attachment slot 1104b, a distal guide slot 1106, an anterior guide slot 1108, and a chamfer guide slot 1110. One side of the attachment slots 1104 is open, so the chamfer cutting guide 1100 can slide onto the bone pins. The attachment slot opening is best visualized in FIG. 11D on the right side of the attachment slots 1104.

Figure 12B:
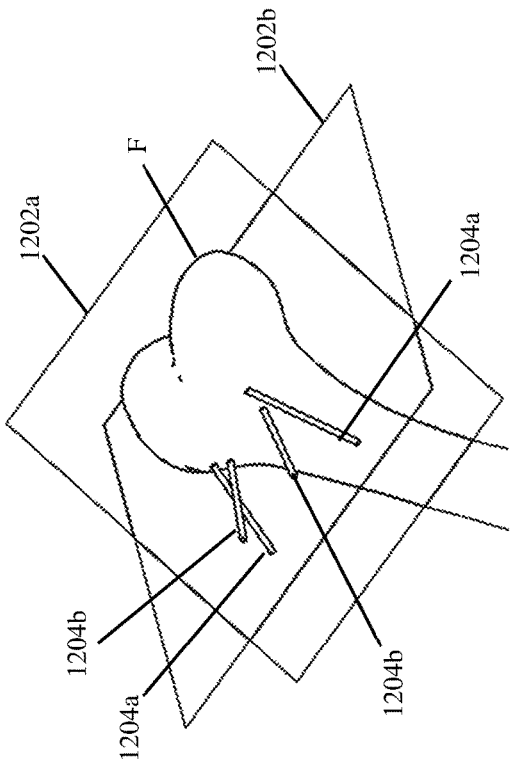
FIGS. 12A-12D illustrate the placement of pins to receive a 5-degree-of-freedom chamfer cutting guide in accordance with embodiments of the invention.
Figure 12A:
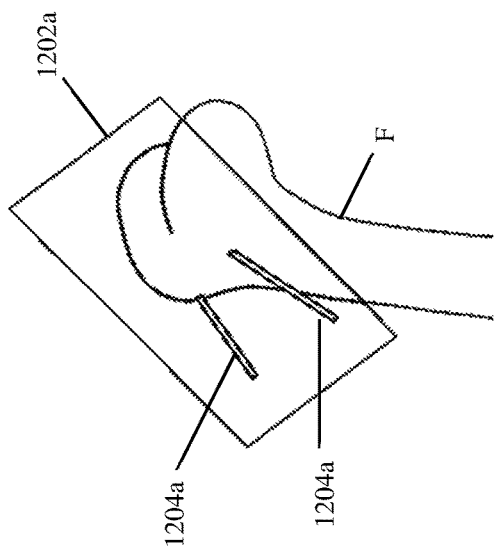
Figure 12D:
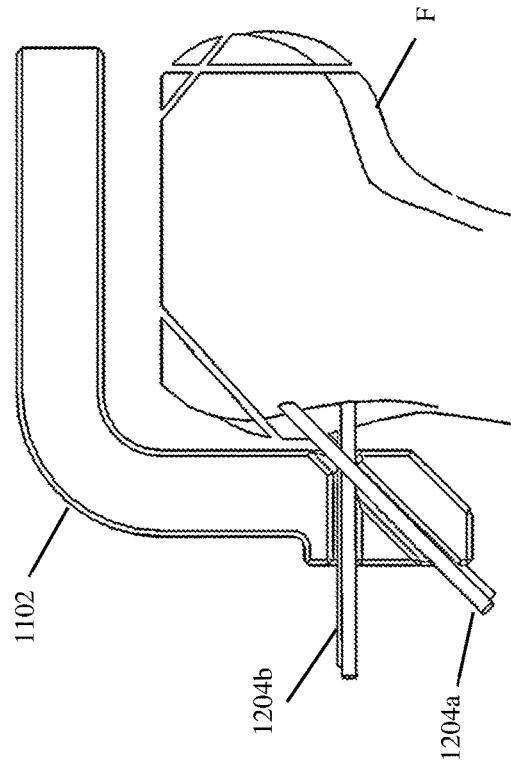

The planning software defines the location of 5-DOF chamfer cutting guide 1100 in the location necessary to place the guide slots in the correct position and orientation to accurately execute the planned cut planes. The surgical plan also includes two pin planes (1202a, 1202b, as shown in FIGS. 12A-12B), on which bone pins (1204a, 1204b) are placed that are defined relative to the cut planes; the two planes have an intersection axis that is parallel to all of the cut planes. The pin planes (1202a, 1202b) may be defined using the known dimensions of the chamfer cutting guide 1100, and the POSE of the planned cut planes. For example, the planning software knows the position and orientation of the attachment slots 1104 with respect to the guide slots. Using these dimensions the planning software may define a first pin plane 1204a and a second pin plane 1204b. By defining two pin planes with four or more pins, 5 degrees of freedom are constrained, which is sufficient to perform a TKA procedure using a surgical saw if the unconstrained degree of freedom is in the medial-lateral direction, which is parallel to all of the cut planes.

Figure 12C:
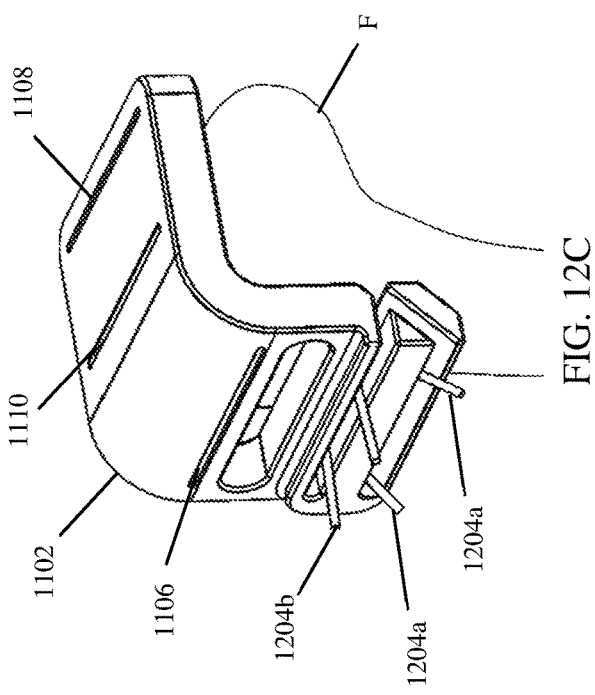

A surgical system, such as the one described above, is then used to place the bone pins (1204a, 1204b) substantially coincident on the pin planes (1202a, 1202b). Once again, the pins 1204 can be inserted at an arbitrary position and orientation on that plane. The attachment slots 1104 of the chamfer cutting guide 1100 slide over the bone pins (1204a, 1204b) as shown in FIG. 12C. The user then creates the distal cut plane, anterior cut plane, posterior cut plane, and the chamfer cut planes by guiding a surgical saw through the respective guide slots. The chamfer guide 1100 and the bone pins 1204 are then removed. A second cut guide (not shown), which fits against the distal and posterior cut surfaces can guide the anterior cut using similar embodiments of the cutting guides, pin planes, and bone pins as described herein.

Pin Alignment Guide

Figure 13B:
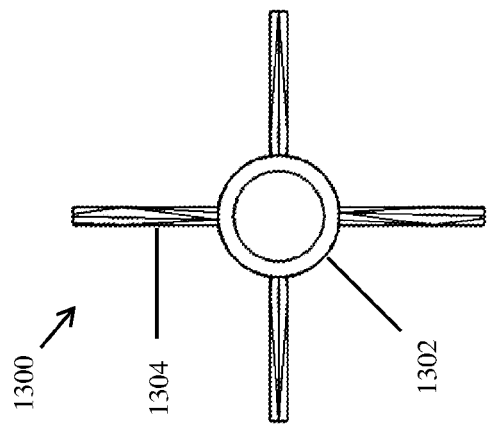
FIGS. 13A and 13B depicts a pin alignment guide for aligning a pin in a specific location on a bone in accordance with embodiments of the invention.
Figure 14B:
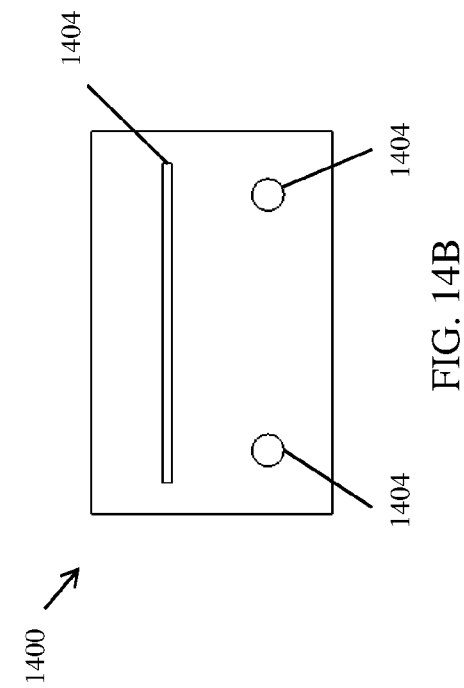
FIGS. 14A and 14B depicts a cutting guide with attachment holes spaced a distance apart in accordance with embodiments of the invention.
Figure 13A:
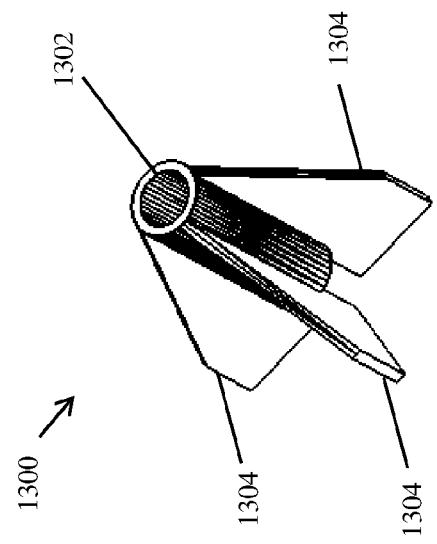
Figure 14A:
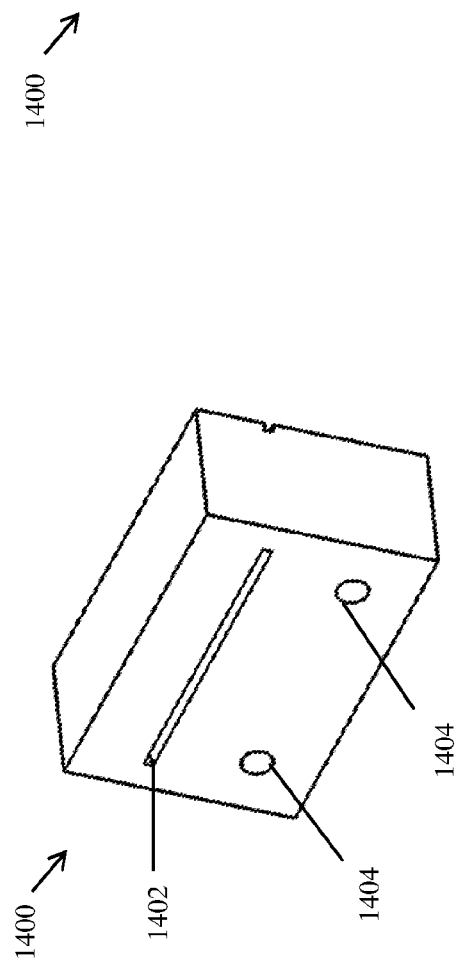

In a particular embodiment of the alignment guide, a pin alignment guide 1300 is shown in FIG. 13A and FIG. 13B. The pin alignment guide 1300 includes a tubular body 1302 and fins 1304 extruding outwardly from the tubular body 1302. The pin alignment guide 1300 aids a user in aligning bone pins for use with a cutting guide that requires the bone pins to be placed a specific distance apart. For example, the cutting guide 1400 shown in FIGS. 14A and 14B includes a guide slot 1402, and two holes 1404 that receive bone pins placed a specific distance apart.

Figure 15B:
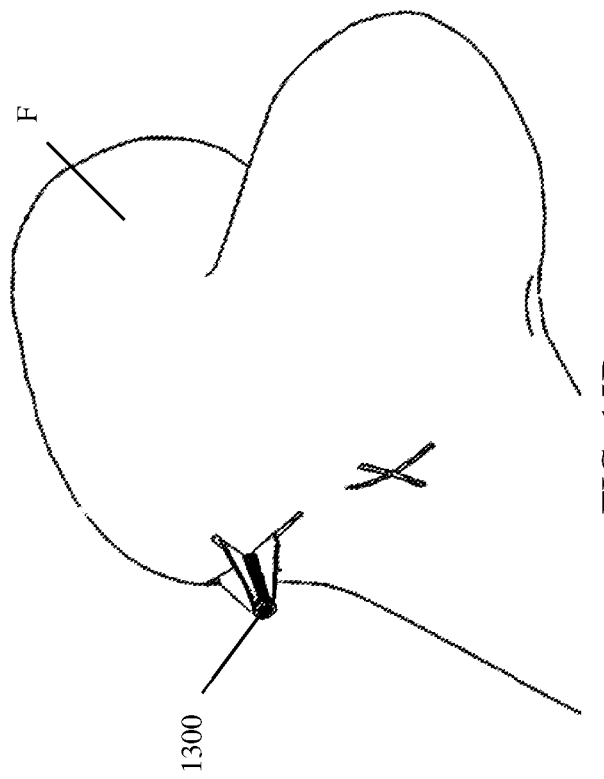
FIGS. 15A and 15B illustrates at least two perpendicular channels created on the bone to receive the pin alignment guide in accordance with embodiments of the invention.
Figure 15A:
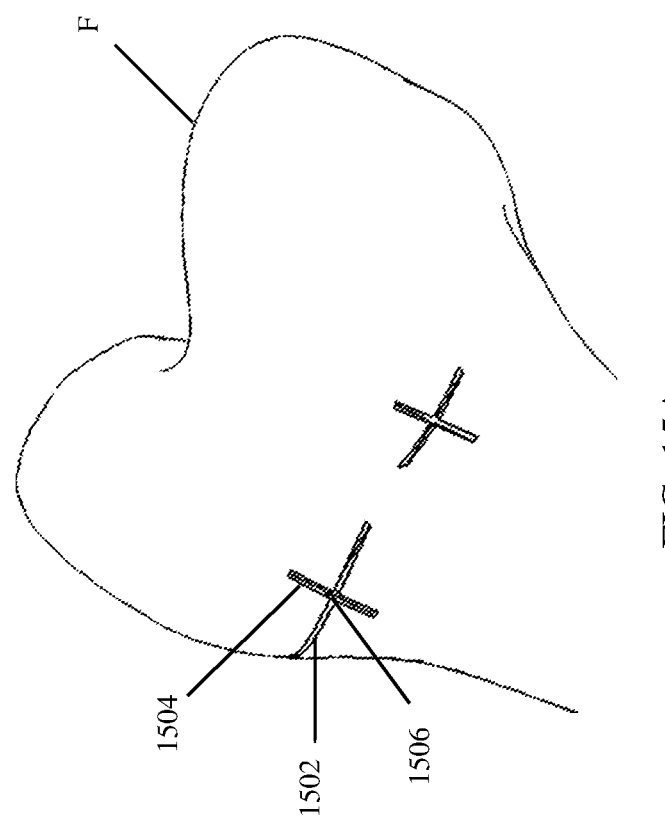

To use the pin alignment guides 1300, with respect to FIG. 15A, at least two perpendicular channel planes are defined in the planning software. A first channel plane, to create a first channel 1502 on the bone, is defined as described above using the planned distal cut plane 310 and the distance between the guide slot 1402 and the center of the holes 1404. A second channel plane, to create a second channel 1504 on the bone, is defined perpendicular to the first channel plane. A third channel plane is defined perpendicular to the first channel plane and medially/laterally translated by the distance between the centers of the holes 1404 of the cutting guide 1400. The channels (1502, 1504) are precisely milled on the bone using a surgical system as described above.

The intersection of the first channel 1502 and the second channel 1504 (shown at 1506), receives the pin alignment guide 1300 as shown in FIG. 15B, wherein the fins 1304 fit directly into the channels. A user can then drill a pilot hole, or a bone pin directly through the tubular body 1302 of the pin alignment guide 1300. The procedure is repeated to place any additional bone pins on the bone. Subsequently, the holes 1404 of the cutting guide 1400 are placed on the bone pins, and the bone cut is created as planned. It should be appreciated that this technique can similarly be used for other cutting guides. For example, the pin alignment guide technique can be used to create pilot holes on the distal cut 416 of the femur F for the pegs 512 of a 4-in-1 block 500.

Tibial Cut Plane

The tibial cut plane may be created using similar embodiments as described above and should be apparent to one skilled in the art after reading the subject matter herein.

In a particular embodiment, the tibial cut guide may be aligned in varus-valgus rotation, internal-external rotation, flexion-extension rotation, and proximal-distal position. The anterior-posterior position is not important. The tibial cut guide is positioned using two or more pins positioned on two planes that have an intersection axis that is aligned with the planned anterior-posterior direction. For example, two planes oriented ±45° in varus-valgus, such that when the guide is placed on the pins, all degrees of freedom except the anterior-posterior are constrained.

Example: Distal Cutting Guide, Alignment Guide and 4-in-1 Block

Testing was conducted on femoral and tibia saw bones using the 2-DOF surgical system 100, the universal distal cutting guide 400, the offset alignment guide 700 and the 4-in-1 block 500. Artificial ligaments were attached between the saw bones to mimic the kinematics of the knee. The purpose of the testing was to assess the overall time required to create the planar cuts on the femoral saw bone, referred to hereafter as femur. The timing began prior to fixing the femoral tracking array 120b and ended once the last cut plane on the femur was completed.

To begin, the femoral tracking array 120b was fixed to the lateral side of the femur. A tracked digitizer probe was used to collect various points on the distal femoral surface. The collected points were used to register the POSE of the femur to a surgical plan. The 2-DOF surgical device 104 was used to drill two holes in the virtual pin plane 414, the virtual pin plane 414 being defined in the planning software prior to testing. A standard drill was then used to insert pins 412 in the drilled holes. The universal distal cutting guide 400 was clamped to the pins 412 and the distal cut 416 was created using a surgical saw guided through the slot 406 of the distal cutting guide 400. The distal cutting guide 400 and pins 412 were then removed from the femur.

The 2-DOF surgical device 104 was then used to mill a channel 800 on the distal cut surface 416 along the virtual channel plane, the virtual channel plane being defined in the planning software prior to testing. The ridge 704 of the offset alignment guide 700 was placed in the channel 800 and a standard drill was used to drill two holes on the distal surface 416 guided by the two holes 604' of the offset alignment guide 700. The offset alignment guide 700 was removed from the channel 800 and the pegs 512 of the 4-in-1 block 500 were placed in the two drilled holes. The remaining four planar cuts were created using a surgical saw guided by the guide slots (504, 506, 508, and 510) of the 4-in-1 block 500. The recorded time from femoral tracking array 120b fixation to the creation of the final cut plane was approximately 18 minutes.

It is worthy to note, that during testing the standard drill had lost power and required charging. The timing was not stopped during the charging step. It is presumed that an experienced surgeon could execute this testing procedure in approximately 10 to 15 minutes.

Articulating Pin-Driving Device

The articulating device 204 of the 2-DOF surgical system 100 described above can accurately align a tool/pin to be coincident with one or more virtual planes. However, the surgeon still has to manually advance the device 204 towards the bone to insert the pin or to create a pilot hole for the pin, which may be uncomfortable for the surgeon. In addition, it is possible that extreme or sudden movements by the surgeon or bone while operating the device may introduce small errors in the pin alignment. A contributing factor to the extreme or sudden movements may be a lacking of real-time information, during use, as to the articulating travel range, or workspace, in which the device operates 204 within.

To provide further control and feedback for the user, the 2-DOF surgical device 104 may be modified to include a third pin-driving degree-of-freedom, which will be referred to hereinafter as an articulating pin-driver device 104'. With reference to FIGS. 18A-18C in which like reference numerals have the meaning ascribed to that numeral with respect to the aforementioned figures, a particular embodiment of the articulating pin driver device 104' is shown. In addition to the components of the 2-DOF surgical device 104, the working portion 204' of the articulating pin driver device 104' further includes components configured to drive a pin 206' into a bone. Specifically, with reference to FIG. 18C, the working portion 204' includes the motor 205, a motor coupler 1808, a pin-driving ball screw 1804, a pin holder 1806, and the pin 206'. A specially adapted carriage 1810 is configured to support and carry the working portion 204' and may include mechanisms for actuating the pin. In some inventive embodiments, the carriage 1810 includes a pin-driving ball nut 1812 and connection members 1814 such as holes, bearings, or axle supports to receive a rod, a dowel, or an axel to act as the hinges (220a, 220b) that are connected with the first end of the linear rails (208a, 208b). The motor coupler 1808 couples the motor 205 with the pin-driving ball screw 1804. The pin-driving ball screw 1804 is in mechanical communication with the pin-driving ball nut 1812. The pin holder 1806 connects the pin-driving ball screw 1804 with the pin 206'. The pin 206' is removably attached with the pin holder 1806 to allow the pin 206' to remain in the bone when inserted therein. The motor 205 may bi-rotationally drive the pin-driving ball screw 1804 and the pin 206' to advance and drive the pin 206' into a bone. The components may further include a motor carriage (not shown) operably connected with a motor linear rail (not shown). The motor carriage is secured to the motor 205 to keep the motor 205 from rotating while allowing the motor 205 to translate along the motor linear rail. The motor linear rail may extend from the carriage 1810. FIG. 18A illustrates the pin 206' in a retracted state and FIG. 18B illustrates the pin 206' in an extended state, where the pin 206' can translate a distance "d2". An outer guard 1802 may be present to guard the user from the actuating mechanisms in the working portion 204'. If an outer guard 1802 is present, the guard 1802 may be dimensioned to conceal the entire pin 206' when the pin 206' is in the retracted state, or the guard 1802 may only conceal a portion of the pin 206' to allow the user to visualize the tip of the pin 206' prior to bone insertion.

In a specific embodiment, the working portion 204' may include a first motor 205 for rotating the pin 206', and a second motor (not shown) for translationally driving the pin 206'. The second motor may rotate a ball screw or a worm gear that is in communication with an opposing ball nut or gear rack configured with the first motor 205. As the second motor bi-rotationally drives the ball screw or worm gear, the first motor 205 and the pin 206' translate accordingly.

The device computer 108 of the articulating pin driving device 104' may further include hardware and software to control the pin-driving action. In an embodiment, the device computer 108 includes two motor controllers for independently controlling the front actuator 210a and back actuator 210b, respectively, to maintain the POSE of the working portion (204, 204'). A third motor controller may independently control the motor 205 for driving and rotating the pin 206' into the bone. In the specific embodiment where a first motor 205 rotates the pin 206' and a second motor (not shown) translates the pin 206', the device computer 108 may include two separate motor controllers to independently control the first motor 205 and the second motor.

In a specific embodiment, with reference to FIGS. 19A-19B, the articulating device 104' includes a bone stabilizing member 1902 attached or integrated with the hand-held portion 202. The bone stabilizing member 1902 includes bone contacting elements (1904a, 1904b) which are configured to contact the bone and stabilize the hand-held portion 202 while the working portion 204' articulates. The bone contacting elements (222a, 222b) may be a flat surface, a pointed protrusion, or a surface having jagged edges to interact with the bone and stabilize the hand-held portion 202. The bone contacting element(s) (1904a, 1904b) project just beyond the working portion 204' such that the element(s) (1904a, 1904b) may contact the bone without negatively impacting how deep the pin 206' may be inserted in the bone. When the user is in the approximate region for driving the pin 206', the user may stabilize the hand-held portion 202 to the bone via the bone contacting elements (1904a, 1904b). With the hand-held portion stabilized, the working portion 204' further articulates until the pin 206' is precisely coincident with a virtual pin plane. In a specific embodiment, once the pin 206' aligns with the virtual pin plane 214, the system 100 automatically locks the actuators (210a, 210b) and activates the motor 205 to drive the pin 206' into the bone. In another embodiment, the user activates a user input mechanism such as a trigger 214 or a button before the system 100 either locks the actuators (210a, 210b), drives the pin 206', or both. Therefore, the user can anticipate and control when the pin 206' is driven into the bone. This user input mechanism may similarly be used by the user to control the amount of extension or retraction of the pin 206' in general.

In a particular embodiment, with reference to FIG. 19A, one or more indicators 1906, such as an LED or a display, is attached or integrated with the device 104'. The indicator 1906 may be attached to the outer guard 1802, the working portion 204', or the hand-held portion 202 for example. The indicator(s) 1906 provide feedback to the user as to a current position of the device 104' with respect to a desired position for the device 104'. For example, the indicator 1906 may emit a red light to indicate that the device 104' is outside of the travel ranges of the three ball screws (216a, 216b, 1804). In other words, a red light is emitted when the working portion 204' and pin 206' can no longer be articulated to reach a desired position, orientation, or a desired depth to insert the pin 206'. The indicator 1906 may emit a yellow light when the user is approaching the travel ranges and a green light when the pin 206' is aligned with a virtual pin plane. The indicator 1906 may further produce a blinking light that changes in blinking frequency based on how close the device 104' is to exceeding the travel range, or how close the pin 206' is to a virtual pin plane. The indicator 1906 may also indicate when the device 104' is ready to autonomously place the pin inside the bone. In a particular embodiment, the working portion 204' does not actuate until the indicator 1906 is in an active state, where the active state is triggered when the device 104' is within the travel limits of the ball screw. This data conveyed by the indicator 1906 is readily available based on either: a) local data collected directly from the device 104', such as the device kinematics; b) the tracking data collected from the tracking system 106; c) a comparison of the POSE of the device 104' with the surgical plan; or d) a combination thereof.

Figure 20B:
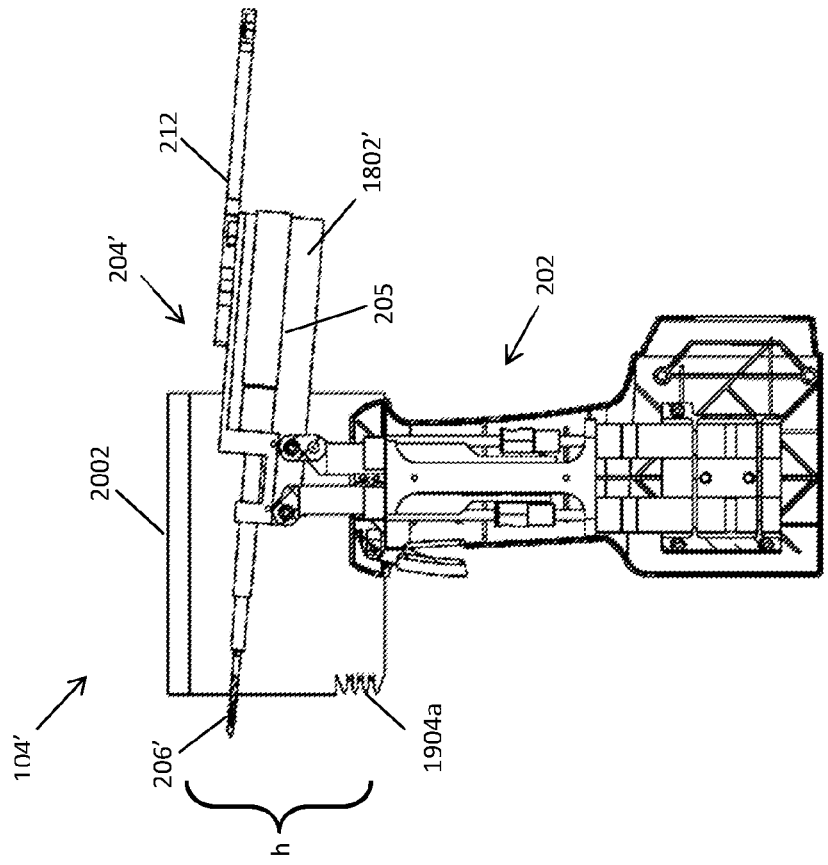
FIGS. 20A and 20B depicts a partial enclosure enclosing the working portion in accordance with embodiments of the invention.
Figure 20A:
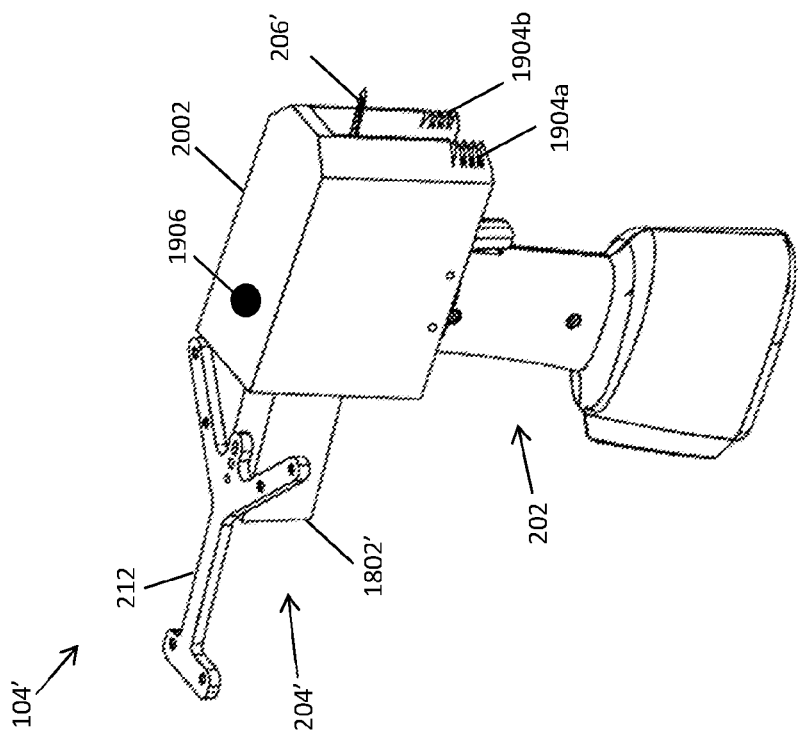

In a specific embodiment, with reference to FIGS. 20A and 20B, the articulating device 104' includes a partial enclosure 2002. FIG. 20A is perspective view of the articulating device 104' with the partial enclosure 2002 and FIG. 6B is a cross-section view thereof. The partial enclosure 2002 is attached to the hand-held portion 202 and partially encloses the working portion 204'. The working portion 204' is able to articulate within the partial enclosure 2002. The partial enclosure 2002 has an internal dimension (i.e. height or diameter) of 'h' that corresponds to the travel range of the working portion 204'. This dimension 'h' may account for the translation 'd' of the working portion 204' and any additional height required to account for the pitch 'α' of the working portion 204'. The advantage of the partial enclosure 2002 is to provide the user with a guide as to the workspace or travel range of the working portion 204'. The user can simply place a front end of the partial enclosure 2002 on the bone to stabilize the hand-held portion 202, at which time the working portion 204' can articulate to a virtual pin plane and drive the pin 206' into the bone. The user is no longer trying to aim the small pin 206' directly to a pin plane, but is rather using a larger guide, the partial enclosure 2002, to get the pin 206' in the general vicinity of a pin plane and allowing the working portion 204' to perform the alignment. In addition, the user no longer has to worry about exceeding the travel limits of the working portion 204' while aligning the pin 206'.

The front end of the partial enclosure 2002 may act as a bone contacting element (1904a, 1904b) to stabilize the hand-held portion 202 and may further include features such as a jagged edge or one or more pointed protrusions.

The pin 206' extends beyond the partial enclosure 2002 in the extended state to allow the pin to be driven into the bone as shown in FIG. 6B. When the pin 206' is in the retracted state, the pin 206' is enclosed within the partial enclosure 2002.

The partial enclosure 2002 may further include the indicator 1906 to aid the user in positioning the device 104' to a desired pin plane as described above.

The partial enclosure 2002 is further configured to allow the tracking array 212 to attach with the working portion 204', or an outer guard 1802' of the working portion 204', to permit the tracking system 106 to track the POSE of the working portion 204' as it articulates.

In a particular embodiment, with reference to FIGS. 21A and 21B, the articulating device 104' includes a full enclosure 2102. FIG. 7A is a perspective view of the articulating device 102 with the full enclosure 2102 and FIG. 7B is a cross-section view thereof. The full enclosure 2102 is configured with the same principles and has the same advantages as the partial enclosure 2002, except the tracking array 212 is attached directly to the full enclosure 2102. Since the tracking array 212 is attached to the full enclosure 2102, the control scheme for controlling the working portion 204' must be modified, where the device kinematics are used to determine the POSE of the working portion 204'. Particularly, the tracking system 106 tracks the hand-held portion 202 based on the geometric relationship between the array 212 and the hand-held portion 202, and the actuator (210a, 210b) positions (i.e. the rotational position of the actuators that corresponds to the position of the ball nuts (218a, 218b) on the ball screws (216a, 216b)) are used to determine the POSE of the working portion 204' with respect to the hand-held portion 202. Therefore, the computing system 102 can determine new actuator positions to control and align the pin 206' with a virtual pin plane.

It should be appreciated that the partial enclosure 2002 and full enclosure 2102 may be sized and adapted for assembly to a hand-held system having greater than two degrees of freedom with similar advantages. For example, it is contemplated that the inner dimensions of the enclosure (226, 228) may accommodate the travel limits of a device having an articulating portion that articulates in one or more translational directions, pitch, and yaw such as the system described in U.S. Pat. App. No. 20130060278. However, as the number of degrees of freedom increase, so does the size of the enclosure (226, 228) which may impede the operating workspace.

It should be further appreciated that the embodiments of the bone stabilizing member 1902, the indicator 1906, the partial enclosure 2002, and full enclosure 2102, can all be adapted for use with the 2-DOF surgical device 104 as shown in FIGS. 2A-2B.

Bi-Cortical Drilling

To further stabilize the bone pins in the bone it may be desirable to drill the pins through two cortical regions of the bone, also referred to as bi-cortical drilling. However, if a drill bit or a pin is drilled beyond the second cortical region and into the soft tissue, patient harm can occur. Therefore, it is proposed that the third pin-driving actuation axis can also be used to retract the drill bit/pin if the drill bit/pin breaks through the second cortical region.

In a particular embodiment, bone breakthrough is detected using an existing method, such as the method described in Taha, Zahari, A. Salah, and J. Lee. "Bone breakthrough detection for orthopedic robot-assisted surgery." *APIEMS* 2008 *Proceedings of the 9th Asia Pacific Industrial Engineering and Management Systems Conference*. 2008, which is hereby incorporated by reference in its entirety. The articulating pin-driving device 104' then automatically retracts the drill bit/pin at a constant optimal retraction speed relative to the bone, regardless of how the user is moving the hand-held portion 202. This ensures that if the drill bit/pin breakthrough the second cortical region, that the drill bit/pin is retracted so as to not cause any patient harm. The retraction speed is a function of the optimal retraction speed combined with the current speed of the hand-held portion 202.

The relative speed between the hand-held portion 202 and the bone can be measured several different ways. In one embodiment, the speed of the hand-held portion 202 relative to the bone is not detected and instead a speed is assumed. In another embodiment, a simple linear distance measuring tool is used, such as a laser distance measurement device. In a particular embodiment, the tracking system 106 is used to track both the bone and the hand-held portion 202 using one or more fiducial markers on each of the bone and the hand-held portion 202.

OTHER EMBODIMENTS

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes can be made in the function and arrangements of elements without departing from the scope as set forth in the appended claims and the legal equivalents thereof.

The foregoing description is illustrative of particular embodiments of the invention, but is not meant to be a limitation upon the practice thereof. The following claims, including all equivalents thereof, are intended to define the scope of the invention.

The invention claimed is:

1. A surgical device for inserting a pin in a bone comprising:
   a hand-held portion;
   a working portion movably connected to the hand-held portion;
   a motor for driving the pin for insertion of the pin in the bone; and
   an actuator system for moving the working portion relative to the hand-held portion in response to control signals corresponding to movement of at least one of the bone and the hand-held portion to maintain alignment of an axis of the pin coincident with a virtual plane having a predetermined location relative to the bone for insertion of the pin in the bone coincident with the virtual plane.

2. The device of claim 1 wherein the surgical device is powered by batteries.

3. The surgical device of claim 1 wherein the virtual plane is oriented with respect to a predetermined location for a cut surface to be created on the bone.

4. The surgical device of claim 3 wherein the virtual plane orientation is offset by a predetermined distance from the predetermined location for the cut surface.

5. The surgical device of claim 4 wherein the predetermined distance is based at least in part on a geometry of a cutting guide.

6. The surgical device of claim 1 further comprising the pin.

7. The surgical device of claim 1 wherein the control signals are generated by one or more computers.

8. The surgical device of claim 7 wherein the one or more computers receive position and orientation (POSE) data from a tracking system indicating a determined POSE of the surgical device.

9. The surgical device of claim 8 further comprising the one or more computers.

10. The surgical device of claim 9 wherein the one or more computers are housed in the hand-held portion.

11. The surgical device of claim 8 wherein the one or more computers wirelessly receive the POSE data from the tracking system.

12. The surgical device of claim 8 wherein the tracking system is an optical tracking system.

13. The surgical device of claim 1 wherein the actuator system comprises a first actuator and a second actuator to move the working portion translation relative to the hand-held portion in response to the control signals.

14. The surgical device of claim 1 wherein the working portion further comprises three or more fiducial markers that are tracked by a tracking system.

15. The surgical device of claim 14 wherein the three or more fiducial markers are on a tracking array and the tracking array is attached to the working portion.

16. The surgical device of claim 1 wherein the motor drives the pin by rotating the pin about the axis of the pin.

17. The surgical device of claim 1 wherein the bone is subject to knee arthroplasty.

\* \* \* \* \*